(12) United States Patent
Heckman

(10) Patent No.: US 7,050,620 B2
(45) Date of Patent: May 23, 2006

(54) METHOD OF ASSAYING SHAPE AND STRUCTURAL FEATURES IN CELLS

(76) Inventor: Carol A. Heckman, 861 Ferndale Ct., Bowling Green, OH (US) 43402

(*) Notice: Subject to any disclaimer, the term of this patent is extended or adjusted under 35 U.S.C. 154(b) by 699 days.

(21) Appl. No.: 10/109,394

(22) Filed: Mar. 28, 2002

(65) Prior Publication Data

US 2002/0164063 A1    Nov. 7, 2002

Related U.S. Application Data

(60) Provisional application No. 60/280,053, filed on Mar. 30, 2001.

(51) Int. Cl.
*G09K 9/00* (2006.01)

(52) U.S. Cl. .................. 382/133; 382/128; 382/129; 382/134; 382/190

(58) Field of Classification Search ........ 382/128–134, 382/181, 199, 266, 190; 435/4, 7.23, 40.51
See application file for complete search history.

(56) References Cited

U.S. PATENT DOCUMENTS

| | | | |
|---|---|---|---|
| 5,902,732 A * | 5/1999 | Hochman | 435/29 |
| 5,978,497 A * | 11/1999 | Lee et al. | 382/133 |
| 2002/0119441 A1* | 8/2002 | Elias | 435/4 |
| 2002/0154798 A1* | 10/2002 | Cong et al. | 382/128 |

OTHER PUBLICATIONS

Heckamn, C.A., PLummer, H.K., III and Runyeon, C.S., Persistant effects of phorbol 12-myristate 12-acetate: possible implication of vasicle traffic. J. Cell Physiol. 166:217-230. 1996.

Holm, P.K., Eker, P., Sandvig, K. and van Deurs, B., Phorbol myristate acetate selectively stimulates apical endocytosis via protein kinase C in polarized MDCK cells. Exp. Cell Res. 217:157-168, 1995.

Heckamn, C.A. and Jamasbim R.J., Describing shape dynamics in transformed rat cells through latent factors. Exp. Cell Res. 246:69-82, 1999.

Olson, M.F., Ashworth, A. and Hall, A., An essential role for Rho, Rac, and Cdc42 GTPases in cell cycle progression through $G_1$, Science 269:1270-1272, 1995.

Kozma, R., Ahmed, S., Best, A. and Lim, L., The Ras-related protein Cdc42Hs and bradykinin promote formation of peripheral actin microspikes and filopodia in Swiss 3T3 fibroblasts. Mol. Cell Biol. 15:1942-1952, 1995.

(Continued)

*Primary Examiner*—Jose L. Couso
*Assistant Examiner*—Tom Y. Lu
(74) *Attorney, Agent, or Firm*—Emch, Schaffer, Schaub & Porcello Co., L.P.A.

(57) ABSTRACT

The method for repetitively determining a profile of quantitative features for different cells in a sample by collecting and analyzing information on the mass distribution in cells or portions of cells and comparing the collected information to values from a relational database is disclosed.

46 Claims, 10 Drawing Sheets

OTHER PUBLICATIONS

Harden, N., Lee, J., Loh, H.-Y., Ohn, Y-M., Tan, I., Leung T., Manser, E. and Lim, L., A*Drosophila* homolog of the Rac- and Cdc42-activated serine/threonine kinase PAK is a potential focal adhesion and focal complex protein that colocalizes with dynamic actin structures, Mol. Cell Biol. 16:1896-1908, 1996.

Heckman, C.A. Campbell, A.E. and Wetzel, B., Characteristic shape and surface changes in epithelial transformation, Exp Cell Res. 169:127-148, 1987.

Plummer, H.K., III, and Heckman, C.A. Transient expression of the transformed phenotupe stimulated by 12-O-tetradecanoyl photbol-13-acetate, Exp Cell Res. 188:66-74, 1990.

Rozengurt, E. and Mendoza, S., Monovalent ion fluxes and the control of cell proliferation in cultured fibroblasts. In: Growth Regulation by Ion Fluxes. vol. 339. Leffert HL (ed). Ann NY Acad. Sci., PP 175-190, 1980.

Roberts, R.L., Nath, J., Friedman, M.M. and Gallin, J.I., Effects of taxol on human neutrophils, J. Immunol. 129:2134-2141, 1982.

Ray, P., Middleton, W. and Berman, J., Mechanism of agonist-induced down-regulation and subsequent recovery of muscarinic acetylcholine receptors in a clonal neuroblastoma X glioma hybird cell line, J. Neurochem. 52:402-409, 1989.

Herman, B. and Albertini, D.F., A time-lapse video image intensification analysis of cytoplsmic organelle movements during endosome tranlocation, J Cell Biol. 98:565-576, 1984.

Herman, B., Langevin, M.A. and Albertini, D.F. The effects of taxol on the organization of the cytoskeleton in cultured ovarian granulose cells, Eur. J. Cell Biol. 31:34-45, 1983.

Brown, D.L. Little, J.E., Chaly, N., Schweitzer, I. And Paulin-Levasseur, M., Effects of taxol on microtubule organization in mouse splenic lymphocytes and on response to mitogenic stimulation, Eur. J. Cell Biol.37:130-139, 1985.

Heckman CA: Cell shape and growth control. Advances in Cell Culture, Maramorosch K, Ed. (Academic Press, N. Y.), 4: 85-156, 1985.

Pitterle, D.M., Sperling R.T., Myers, M.G., Jr., White, M.F. and Blackshear, P.J., Early biochemical events in insulin-stimulates fluid phase endocytosis, Am J. Physiol. 276:E94-E105, 1999.

Hedin, U. and Thyberg, J., Receptor-mediated endocytosis of immunoglobulin-coated colloidal gold particles in cultured mouse peritoneal macrophages. Chloroquine and monensin inhibit transfer of the ligand from endocytic vesicles to lysosomes, Eur. J. Cell Biol. 39:130-135, 1985.

Porpaczy, Z., Tomasek, J.J. and Freeman, D.A., Intemalized plasma membran cholesterol passes through an endosome compartment that is distinct from the acid vesicle-lysosome compartment, Exp Cell Res. 234;217-224,1997.

Wolkoff, A.W., Klausner, R.D., Ashwell, G. and Harford, J., Intracellular segration of asialoglycoproteins and their receptor: a prelysosomal event subsequent to dissociation of the ligand-receptor complex, J Cell Biol. Chem. 98:375-381, 1984.

Jin, M. and Snider, M.D., Role of microtubules in transferring receptor transport from the cell surface to endosomes and the Golgi complex, J. Biol. Chem. 268:18390-18397, 1993.

Stenseth, K. and Thyberg, J., Monensin and chloroquine inhibit transfer to lysosomes of endocytosed macromolecules in cultured mouse peritoneal macrophages, Eur. J. Cell Biol. 49:326-333, 1989.

Sheetz, M.P. and Yu, H., Regulation of kinesin and cytoplasmic dyneindriven organelle motility, Semin. Cell Dev. Biol. 7:329-334, 1996.

Touzani, K., Alvarado, F. and Vasseur, M., pH gradient effects on chloride transport across basolateral membrane vesicles from guinea-pig jejunum, J. Physiol. 500:385-400, 1997.

Goltz, J.S., Wolkoff, A.W., Novikoff, P.M., Stockert, R.J. and Satir, P., A role for microtubules in sorting endocytic vesicles in rat hepatocytes, Proc. Natl. Acad. Sci. USA 89:7026-7030, 1992.

Thatte, H.S., Bridges, K.R. and Golan, D.E., Microtubule inihibitors differentially affect translational movement, cell surface expression, and endocytosis of tranferring recpetors in K562 cells, J. Cell Physiol. 160:345-357, 1994.

Hicke, L., Zanolari, B., Pypaert, M. Rohrer, J. and Riezman, H., Transport through the yeast endocytic pathway occurs through morphologically distinct compartments and requirs an active secretory pathway and Sec 18p/N-ethylmaleimide-sensitive fusion protein, Mol. Biol. Cell 8:13-31, 1997.

Erickson, J.W., Zhang, C., Kahn, R.A., Evans, T. and Cerione, R.A., Mammalian Cdc42 is a brefeldin A-sensitive component of the Golgi apparatus, J. Biol. Chem. 271:26850-26854, 1996.

Lim, L., Manser, E., Leung, T. and Hall, C., Regulation of phosphorylation pathways by p21 GTPases: The p21 Ras-related Rho subfamily and its role in phosphorylation signaling pathways, Eur. J. Biochem. 242:171-185, 1996.

Aspenström, P., Effectors for the Rho GTPases, Curr. Opin. Cell Biol. 11:95-102, 1999.

Kolodney, M.S. and Elson, E.L., Contraction due to microtubule disruption is associated with increased phosphorylation of myosin regulatory light chain, Proc. Natl. Acad. Sci. USA 92:10252-10256, 1995.

Ren, Y., Lin, R., Zheng, Y. and Busch H., Cloning and characterization of GEF-H1, and microtubule-associated guanine nucleotide exchange factor for Rac and Rho GTPases, J. Biol. Chem. 273:34954-34960, 1998.

Gunderson, F.G. and Cook, T.A., Microtubules and signal transduction, Curr. Opin. Cell Biol. 11:81-94, 1999.

Grant, N.J. and Aunis, D., Effects of phorbol esters on cytoskeletal proteins in cultured bovine chromaffin cells: induction of neurofilament phosphorylation and reorganization of actin, Eur. J. Cell Biol. 52:36-46, 1990.

Downey, G.P., Chan, C.K., Lea, P., Takai, A. and Grinstein, S., Phorbol ester-induced actin assembly in neutrophils: role of protein kinase C, J. Cell Biol. 116:695-706. 1992.

Myrdal, S.E. and Auersperg, N., An agent or agents produced by virustransformed cells cause unregulated rufflin in untransformed cells, J. Cell Biol. 102:1224-1229, 1986.

Lopez, I., Burns, D.J. and Lambeth, J.D., Regulation of phospholipase D by protein kinase C in human neutrophils. Conventional isoforms of protein kinase C phosphorylate a phospholipase D-related component in the plasma membrane, J. Biol. Chem. 270:19465-19472, 1995.

Yamazaki, M., Zhang, Y., Watanabe, H., Yokozeki, T., Ohno, S., Kaibuchi, K., Shibata, H., Mukai, H. Ono, Y., Frohman, M.A. and Kanaho, Y., Interaction of the small G protein RhoA with the C terminus of human phopholipase D1, J. Biol. Chem. 274:6035-6038, 1999.

Schonhorn, J.E., Akompong, T. and Wesslingresnick, M., Mechanism of tranferrin receptor down-regulation in K562 cells in response to protein-kinase-C activation, J. Biol. Chem. 270:3698-3705, 1995.

Schmalzing, G., Richter, H.P., Hansen, A., Schwarz, W., Just I and Aktories K: Involvement of the GTP-binding protein Rho in constitutive endocytosis in *Xenopus laevus* oocytes, J. Cell Biol. 130:1319-1332, 1995.

Swanson, J.A., Yirinec, B.D. and Silverstein, S.C., Phorbol esters and horseradish peroxidase stimulate pinocytosis and redirect the flow of pinocytosed fluid in macrophages, J. Cell Biol. 100:851-859, 1985.

Zacharias, U., He, C-J., Hagége, J., Xu, Y., Sraer, J-D, Brass L.F. and Rondeau, E., Thrombin and phorbol ester induce internalization of thrombin receptor of human mesangial cells through different pathways, Exp. Cell Res. 216:371-379, 1995.

Niedergang, F., San-Jose, E., Rubin, B., Alarcon, B., Dautry-Varsat, A. and Alcover, A., Differential cytosolic tail dependence and intraceullular fate of T-cell receptors internalized upon activation with superantigen or phorbol ester, Res. Immunol. 148:231-245, 1997.

Ouyang, X.M., Gulliford, T., Huang, G.C. and Epstein, R.J., Transforming growth factor-alpha short-circuits downregulation of the epidermal growth factor receptor, J. Cell Physiol. 179:52-57, 1999.

Ouyang, X.M., Epstein, R.J., and Gulliford, T., The duration of phorbol-inducible ErbB2 tyrosine dephosphoryation parallels that of receptor endocytosis rather than threonine-686 phosphorylation: implications of the physioloigical role of protein kinase C in growth factor receptor signaling, Carcinogenesis 19:2013-2019, 1998.

Luo, Z.R. and Robinson, J.M., Colocaliztion of an endocytic marker and acid-phophatases in a tubular reticular compartment in marcophages, J. Histochem, Cytochem.40: 93-103, 1992.

Ruegg, C.L., Rajasekar, S., Stein, B.S. and Engleman, E.G., Degradation of CD4 following phorbol-induced internalization in human lymphocytes-T: evidence for distinct routing of CD4 and CD3, J. Biol. Chem. 267:18837-18843, 1992.

Kandror, K.V. and Pilch, P.F., Multiple endocomal recycling pathways in rat adipose cells, Biochem. J 331:829-835, 1998.

Allen, L.A. and Aderem, A., Protein kinase C regulates MARCKS cycling between the plasma membrane and lysosomes in fibroblasts. EMBO J. 14:1109-1120, 1995.

Grinde, B., Effect of carboxylic ionophores on lysosomal protein degradation in rat hepatocytes, Exp. Cell Res. 149:27-35, 1983.

Rabkin, R., Hamik, A., Yagil, C., Hamel, F.G. Duckworth, W.C. and Fawcett, J., Processing of 125l-insulin by polarized cultured kidney cells, Exp. Cell Res. 224:136-142, 1996.

Collins, C.A. and Vallee, R.B., Temperature-dependent reversible assembly of taxol-treated microtubules, J. Cell Biol. 105:2847-2854, 1987.

De Brabander, M., Geuens, G., Nuydens, R., Willebrords, R. and De Mey, J., Taxol induces the assembly of free microtubules in living cells and blocks the organizing capacity of the centrosomes and kinetochores, Proc. Natl. Acad. Sci, USA 78:5608-5612, 1981.

White, Morris F. and Kahn, C. Ronald, The insulin signaling systems, J. Biol. Chem., vol. 269, No. 1, pp. 1-4, 1994.

Heidenreich, K.A., Zeppelin, T. and Robinson, L.J., Insulin and Insulin-like growth factor I induce *c-fos* expression in postmitotic neurons by a protein kinase C-dependent pathway, J. Biol. Chem. 268:14663-14670, 1993.

Heckman CA, Vroman L and Pitlick A: The nature of substrate-attached materials in human fibroblast cultures: localization of cell and fetal calf serum components. Tissue Cell 9:317-334, 1977.

Olson AC, Larson NM and Heckman CA: Classification of cultured mammalian cells by shape analysis and pattern recognition. Proceedings National Academy Sciences USA 77: 1516-1520, 1980.

Kozma, R, Ahmed, S, Best, A, and Lim, L:The Ras-related protein Cdc42 Hs and bradykinin promote formation of peripheral actin microspikes and filopodia Swiss 3T3 fibroblasts. Mol Cell. Biol. 15: 1942-1952, 1995.

Nobes, CD and Hall, A: Rho, rac, and cdc42 GTPases regulate the assembly of multimolecular focal complexes associated with actin stress fibers, lamellipodia, and filopodia. Cell 81: 53-62, 1995.

Kozma, R, Sarner, S, Ahmed, S, and Lim, L: Rho family GTPases and neurolnal growth cone remodeling: relationship between increased complexity induced by Cdc42Hs, Rac1, and acetylcholine and collapse induced by RhoA and lysophosphatidic acid, Mol. Cell. Biol. 17: 1201-1211, 1997.

Zaho, Z-S, Manser, E, Chen, X-Q, Chong, C, Leung, T, and Lim, L: A conserved negative regulatory region in aPAK: Inhibition of PAK kinases reveal their morphological roles downstream of Cdc42 and Rac1. Mol. Cell Biol. 18: 2153-2163, 1998.

Campone, P., Fumoleau, P., Delecroix, V., Deporte-Fety, R., Perrocheau, G., Vermillet, L., Borg-Olivier, O., Louboutin, J. P., Bissery, M. C., Riva, A., Azli, N., 2001, "Phase I dose-finding and pharmacokinetic study of docetaxel and vinorelbine as first-line chemotherapy for metastiatic breast cancer" Annals Oncology 12: 909-918.

* cited by examiner

| Position in Cell | Factor Number | Value increases with: | IAR20PC1 | 1000W |
|---|---|---|---|---|
| upper | 1 | Coarse protrusions or deeply eroded features affecting upper part of cell | ↓a, b | (↓)a |
| upper | 2 | Size of projections on either of the upper two contours (bumpiness) | ← | → |
| global | 3 | Elliptical shape of the whole cell | (↑)a | → |
| edge | 4 | Number of sharp, tapering features at the cell edge (filopodia) | → | → |
| global | 5 | Presence of blunt or sprawling projections or enlarged invaginations at cell edge (mass displacement) | ← | (↓) |
| edge | 7 | Size of knobby projections at the cell edge | ← | (↑) |
| second | 8 | Presence of spiky structures in the second contour | (↓)a | → |
| second | 11 | Variance in size of projections in the second contour | ← | (↑) |
| global | 12 | Rounding-up of the cell | ← | ← |
| second | 13 | Size of hollowed out regions in the second contour | → | ← |
| edge | 16 | Variance in size of projections at the cell edge | → | → | aFactor entered into the equation for solving the transformed type with a sign opposite that shown. bFactors in bold type are used in the equation for the designated cell line. cFactors that are poorly correlated with time in Pearson's product-moment test ($P \geq 0.05$) are shown in parentheses.

Fig. 5 Table 1

Fig. 6 Table 2

| Factor: Definition | No. | Change | Treatment: Ionophores/Weak Bases | | | | Microtubule Inhibitors | | | | | | Tumor Promoter |
|---|---|---|---|---|---|---|---|---|---|---|---|---|---|
| | | | GRA | QUI | VAL | CHL | COL | TAX | CEPH | TX/C | CE/C | DEO | PMA |
| CELL EDGE | | | | | | | | | | | | | |
| filopodia | 4 | ↓ | ↓[a] | no | ↓, no[b] | no[c] | ↓, no | no | no | no | no | no | |
| | 4 | ↓ | | no | no | no | no | no | no | no | no | no | no |
| 1000 W displacement | 5 | ← | no | no | no | no | no | no | no | no | no | no | |
| knob-like | 7 | ← | ← | no | no | no | no, ← | no | ← | no | no | no | |
| 1000 W sharpness | 7 | ← | | no | no | no | ↓, no | no | | no | no | no | ←, no |
| | 16 | → | | no | no | no | no | no | | no | no | no | →, no |
| UPPER CELL | | | | | | | | | | | | | |
| displacement | 1 | → | no | no | no | no | no | no, → | → | no, → | → | → | no |
| 1000 W | 1 | → | | no | no | no | ←, ↑ | no | no | no | no | no | no |
| bumpiness | 2 | → | | no | no | no | no | no | no | no | no | no | no |
| spikes (2nd) | 8 | → | no | no | no, → | no | no | no | no | no | no | no | no |
| variance (2nd) | 11 | ← | | no | no | no | no | no | no | no | no | no | |
| hollows (2nd) | 13 | → | no | no | no | no | no | no | no | no | no | no | |
| GLOBAL | | | | | | | | | | | | | |
| ellipticity | 3 | ← | | no | no | no | no | no | no | no | no | no | no |
| rounding up | 12 | ← | no | no | no | no | no, → | no | no | no | no | no | |
| 1000 W | 12 | ← | no | no | no | no | ↑, no / no, ↑ | no | no | no | no | no | no |

[a] Mean value for the treatment differs from control in Tukey's Studentized range test at $p = 0.05$. [b] If more than one experiment was analyzed and the results differed, both results are given. [c] Values shown in bold type represent the results of two experiments. GRA, gramicidin; QUI, quinidine sulfate; VAL, valinomycin; CHL, chloroquine; COL, colchicine; TAX, paclitaxel; CEPH, cephalomannine; TX/C paclitaxel and colchicine; CE/C, cephalomannine and colchicine; DEO, 7-deoxytaxol; PMA, phorbol myristic acetate.

| Variable Name (in order of correlation with factor #4) | Direction of Change in Transformed Cells | Experimental Treatment: Paclitaxel | | Paclitaxel/Colch | |
|---|---|---|---|---|---|
| | | Cell Line: IAR20 PC1 | 1000 W | IAR20 PC1 | 1000 W |
| PTOM | ↓ | ---[a] | -↑[b] | --↑ | -↑↑ |
| PSHR | ↑ | ↑-- | -↓ | --- | --- |
| SHPF | ↓ | ↓-- | -↑ | --- | -↑↑ |
| FRNC | ↓ | -↓- | -- | --- | --- |
| CSQD | ↓ | ↓-↓ | -↑ | -↑- | --↑ |
| MAXP | ↓ | --- | -↑ | --- | --- |
| WDTH | ↑ | ↑-↑ | -- | --- | ↓-↓ |
| ASHR | ↓ | --- | -↑ | --- | -↑- |

[a] Same change represented in three experimental samples. [b] Changes were statistically significant at p = 0.02. PTOM, perimeter normalized to major axis of the ellipse of concentration; PSHR, perimeter of minimum convex envelope; SHPF, square of perimeter normalized to contour area; FRNC, fraction of contour represented in negative curvature regions; CSQD, square of summed curvature values normalized to number of points on contour; MAXP, area of polygon formed by joining local maxima on contour; WDTH, mean width at base of tapering projections modeled as a triangle; ASHR, area included within minimum convex envelope.

Fig. 7 Table 3

NONC
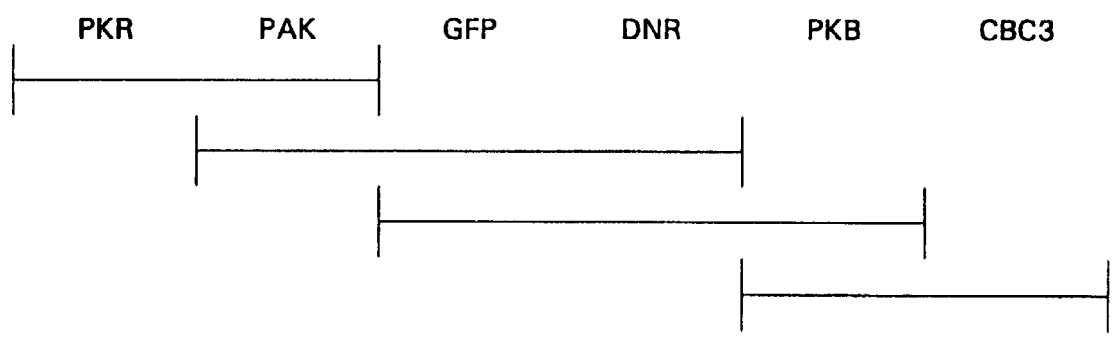
CSQD
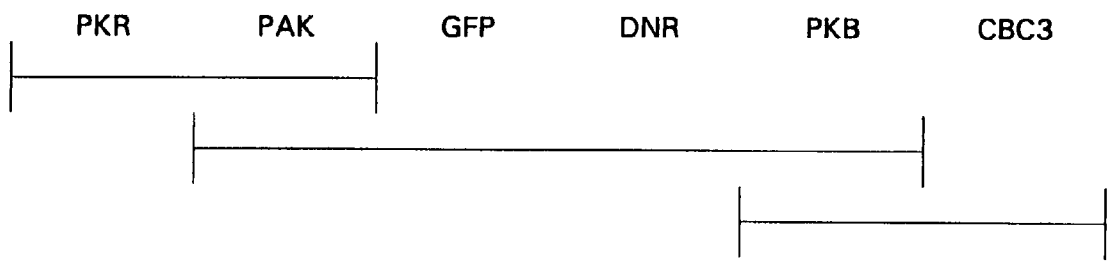
Fig. 9

METHOD OF ASSAYING SHAPE AND STRUCTURAL FEATURES IN CELLS

This application claims benefit of U.S. Provisional Application No. 60/280,053, filed Mar. 30, 2001.

TECHNICAL FIELD

This invention relates to a process for assaying the shape features of cells in order to determine whether the shape features are altered by exposure of the cells to a pharmaceutical or biological agent.

BACKGROUND OF THE INVENTION

There are three types of structural components of cells that become organized in certain ways to regulate cell architecture. These are actin filaments of approximately 8-nm diameter, intermediate filaments of approximately 10-nm diameter, and microtubules (MTs) of approximately 24-nm diameter. Larger macromolecular assemblages are composed from combinations of these smaller structures, which can either aggregate with components like themselves or with adaptor molecules or with other components which causes them to form an assemblage of cytoskeletal molecules. Such processes cause the assemblages to form a metastable cell structure that is easily within the resolving power of the light microscope. Moreover, organelles within the cells are themselves positioned by one or more processes that regulate trafficking along the cytoskeletal components.

Phase microscopic techniques are used to amplify the weak contrast inherent in cells and make visible macromolecular assemblages such as those described above. The phase principle relies upon a small increment of contrast being introduced when the material of the cells, which has an altered refractive index over the aqueous medium, shifts the phase of a light wave by about one-quarter. When the shifted waves are recombined with unshifted waves from the same optical source, cells and tissues can be visualized. However, phase microscopy has the drawback that only small variations in contrast are introduced by cell structure. Variations as great or greater than those introduced by the cells may be introduced by inhomogeneities in the material substrate or by particles floating in the medium. Furthermore, the places where such artifacts contribute to image intensity are unpredictable. This limits the value of the phase technique for the purpose of acquiring images and quantifying variations in their intensity.

The weak contrast variations inherent in phase microscope images were enhanced by the method of video-enhanced differential interference contrast microscopy. This technique enabled people to view and interpret dynamic events that happen in real time by using thin preparations of cells themselves or components extracted from cells. By exploiting analog video-based methods of amplifying contrast, the technique made certain macromolecular assemblages apparent, which are otherwise not visible by light microscopy. A limit on visibility of macromolecular assemblages inside the cell is set by the sample thickness. Thick samples give rise to images that are too complex to interpret due to their overlapping planes of imaged structure, which planes are all projected onto the two-dimensional plane of an image. Therefore, the usefulness of analog, video-based methods for amplifying phase shift-induced contrast is limited to specimens thinner than a cell.

To overcome the limitation imposed by projecting many overlapping layers, each of which contains significant structural details, onto a two-dimensional image plane, principles of confocal microscopy were developed. These principles were reduced to practice by Egger and Davidovits at Yale, by Shephard and Wilson in Oxford, and by Brakenhoff and coworkers in Amsterdam (Scanning 10: 128–138). By making optical sections through the whole thickness or a portion of the thickness of a specimen, confocal microscopes contrive to break down the three-dimensional (3D) information contained in a cell into a series of image planes. These planes may be spaced as little as a fraction of a micron apart. When a number of such planes are collected throughout the thickness of a cell, this enables the viewer to see the relationship between structures for which information may be found in two or more separate planes.

The relationship between structures in separate confocal planes is visually inspected by rotating the planes together as an object in a high-speed digital computer. Alternatively, a person can flip through the planes, which are thereby represented as a moving picture or "fly through" of the image. Nevertheless, one who wishes to automate the analysis of cell structures must apply algorithms that work on the 3D content of the image dataset. Except for those few examples where software has been developed to address specific problems, the availability of such algorithms is very restricted. Practitioners of the art in this field have not developed or refined algorithms for specification and relation of the content of multiple planes in such datasets to each other. To overcome this limitation, such practitioners would need to automate the recognition of different cell components in the datasets. They would need to understand many of the principles regulating the relationship among cell components and how such relationships are changed. As the state of the art does not include such an understanding, progress in this type of problem requires further research.

Some researchers have used a microscope-based scanner, controlled by a motor driven stage, to provide a digitized signal from a sensor. Here, the digitized signals are processed in order to automatically recognize cells while the sample is being scanned. The type of features recognized include such physical characteristics as light scatter, refractive index, and optical density and dimensions such as cell diameter and width. Mathematical transformations of the signal such as Fast Fourier transform, convolution, correlation, etc. can also be performed (U.S. Pat. No. 4,700,298, "Dynamic Microscope Image Processing Scanner"). Although images may be collected using a microscope-based scanner, the majority of reports issued in recent years have utilized other means of image acquisition. One group of investigators employed a television camera to acquire the images (U.S. Pat. No. 4,453,266, "Method and Apparatus for Measuring Mean Cell Volume of Red Blood Cells"), whereas a commercial image analysis system was used in another (U.S. Pat. No. 6,025,128, "Prediction of Prostate Cancer Progression by Analysis of Selected Predictive Parameters").

While the numerous advances in imaging referred to above, have been reduced to practice, they still fall short of being able to represent the complex matter composing a cell in a form that is useful for assaying the shape of cultured cells. The arrangement of any single ingredient of a cell may now be presented in the full 3D coordinate space representing the cell in a high-speed digital computer, but there are hundreds or thousands such molecules mediating the shape of a cell, and so this increases the complexity of the analysis rather than reducing it. To develop methods that are amenable to interpretation and to make up an assay for studying shape properties relevant to problems of biomedical significance, practitioners of the art have ignored advances such as video-enhanced contrast and confocal microscopy. They have instead used a two-dimensional projection of the 3D structure of a cell in the light microscope. One group of investigators developed a system for classifying cells, using histological preparations of cells. A patient's cancerous tissue was used to classify cells, where the objective was to improve prognosis and predict whether the patient's disease would progress to malignant disease. Chromatin texture data were extracted from images of cell nuclei in tissue stained with Feulgen: stain or with hematoxylin and eosin (U.S. Pat. No. 6,025,128). Shape factors were used to describe the shape of cancer cell nuclei. The inventors also claimed the use of training against samples from patients who were known progressors and non-progressors. The results were used as a basis of predicting prostate cancer progression in unknown samples from patients. Training was implemented by a neural network.

The cells in tissue samples are crowded together and cannot be readily distinguished from one another at the boundaries; thus, in the prostate example, variables for shape and entropy are calculated based solely on the shape of the cell nucleus. Since cells in cytological samples and cell cultures are sometimes found entirely separate on a flat substratum, each can be seen in its entirety. If such a sample is viewed with adequate contrast and resolution, some cell shape features and details at the cell edge can be resolved. Three shape features were disclosed by Bacus (U.S. Pat. No. 4,199,748, "Automated Method and Apparatus for Classification of Cells with Application to the Diagnosis of Anemia"). Here, a shape circularity factor was calculated by comparing the square of the number of pixels on the perimeter to the area, measured in the number of pixels enclosed by the boundary. Two additional shape factors, namely the number of "spicules" on the boundary and the comparison of orthogonal boundary chain code orientations, were also computed. Similar shape variables were disclosed in other patents, but these inventors disclosed only a small number of such variables.

Measurements based on the absorbance or optical density of a cell following staining, as disclosed in the above-claimed inventions, had the major drawback that the colors and intensity conferred by a stain could vary due to the irreproducibility of reagents. For example, compounds used to make up different lots of the stain can vary, as can the nature of trace elements and compounds in the water used to dilute the reagents and rinse the specimens. An additional drawback of such methods is that they project the 3D image of a cell into a two-dimensional plane, which means that it is impossible to tell whether any given portion of a cell is thicker than usual or molecules are merely more dense in that portion of the cytoplasm. Whereas it is apparent from the prior art that the shapes of cells or portions of cells can be detected and quantified, the prior work did not develop an analysis of cell shape in detail or at high resolution. To overcome this drawback, while still dealing with the difficulty that few algorithms exist which can relate cell components to one another, the inventor developed a method for analyzing shape features in more detail than previously done by other workers.

Methods for Shape Analysis: To improve contrast and resolution in cultured cell specimens, investigators have used anodic oxide interferometers. These substrates consist of a glass slide coated with a metal which is then anodized so as to form an oxide film insulating the metal. One can view selective interference on such anodic oxide interferometers by using reflected light on a light microscope equipped with appropriate optics. A multi-colored image of the cell is established, owing to the high refractive index of the oxide introducing destructive interference in certain wavelengths. In white light, which contains waves of different lengths, a long wave may travel through an oxide layer which is on the order of a fraction of the wavelength in thickness. Upon reflection off the metal, this wave combines with incoming waves to introduce partial destructive interference. A shorter wave, however, whose path through the thickness of oxide layer corresponds to the distance of one wavelength, shows a completely destructive interference effect. Thus, when a dielectric layer on the size order of a cell is adsorbed to the interferometer, the pattern of interference shows attenuation of the light in some wavelengths and cancellation of the light in others (72). Because the interference pattern is changed by even a thin layer of material, the margins of the cell can be visualized in high contrast. Moreover, the thickness of the cell causes a repetition of interference orders and provides information about the shape of the cells in the third dimension, namely height (73).

The interference method enhanced resolution to such an extent that the investigators could measure the values of numerous shape variables, calculate equations for several model figures, and render 35 of the shape variables dimensionless (74). Said variables were descriptive of the following mathematical values:

1. OCNT=Number of interference contours
2. SHPF=Perimeter squared/area of the contour
3. PTOM=Perimeter/2×major axis
4. AXRT=Length of major axis of ellipse/length of minor axis
5. ARAT=Area of ellipse of concentration normalized to area of the contour
6. AFRN=Area of contour/area of lowermost interference contour
7. DCNT=Distance between highest point and centroid of ellipse of concentration
8. ANGL=Angle formed between major axis and a line joining the DCNT points
9. CURV=(Perimeter/number of points)×summed curvature values
10. CSQD=(Number of points)−1×(summed curvature values)2
11. NONC=Number of negative curvature regions normalized to perimeter length
12. FRNC=Length of perimeter in negative curvature normalized to perimeter length
13. LNNC=Mean length of negative curvature normalized to length of major axis
14. SDNC=Standard deviation of LNNC values
15. BMPS=Number of minor projections on perimeter normalized to perimeter length
16. MEDN=Mean length of projection medians normalized to length of major axis
17. SDMD=Standard deviation of MEDN
18. ALTI=Mean altitude of projections normalized to length of major axis
19. SDAL=Standard deviation of ALTI values
20. WDTH=Mean width of projections at base normalized to length of major axis
21. SDWD=Standard deviation of WDTH values
22. MDAL=Ratio of median length/altitude of projections
23. CENT=Mean distance from centroid to perimeter normalized to length of major axis
24. SDCD=Standard deviation of CENT 25. FOCI=Mean distance from foci to perimeter normalized to length of major axis
26. SDFD=Standard deviation of FOCI
27. FINE=Area of contour included in ellipse normalized to area of the contour
28. MAXP=Area of polygon formed from local maxima normalized to area of the contour
29. MINP=Area of polygon formed from local minima normalized to area of the contour
30. ASHR=Area of minimum convex envelope normalized to area of the contour
31. PSHR=Perimeter of minimum convex envelope normalized to perimeter length
32. CAVS=Number of major concavities in perimeter normalized to perimeter length
33. ACAV=Mean area of the concavities normalized to area of minimum convex figure
34. CVSD=Standard deviation of ACAV
35. LCAV=Area of largest concavity normalized to area of minimum convex figure To test the robustness of the information generated by these methods, the investigators computed values for the shape variables of cells from different cell lines, based on the interference images described above, and used them to form natural groupings. For three epithelial lines studied, there was a striking correspondence between these groups and the actual cell lines of origin (74). Clonally derived populations originating from the same cell line showed a great deal of overlap, whereas cell lines obtained by distinct techniques, albeit from the same tissues, showed far less overlap. When cells were classified by means of principal components, the results appeared superior to those obtained by other methods, such as hierarchical clustering. In principal components classification, only 6% of cells from one lineage overlapped with a those from a cell line having a completely distinct origin (72). Finally, the investigators employed the values of shape variables to create a database representing typical samples from normal and oncogenically transformed rodent cells (7). The concept of training against known samples, disclosed by others as indicated above (U.S. Pat. No. 6,025,128) was also applied by the current investigators to predict the characteristics of an unknown sample of cells. To classify the unknowns, the investigators merely needed to compute the values of variables for shape features and compare them to corresponding values for the known samples that were stored in the database (9).

One of the drawbacks of the classification method was that, although the shape variables were precise in the mathematical sense, they had little intuitive relationship to the shape features of a cell on a one-to-one basis. This meant that the investigators might recognize a sample of cells as having the overall signature of a transformed or a nontransformed population, but not be able to distinguish among their morphological features those ones that conferred the signature values. Because some of the mechanisms of transformation involve GTPases which regulate formation of actin-based features such as filopodia, microspikes, ruffles, and stress fibers, a method of relating said morphological features to the overall phenotype was of particular interest. When values of shape variables were combined through a method called latent factor extraction, new variables were created which incorporate weighted representations of the values of the original variables. In applying it to the training sets, i.e., known transformed and nontransformed cells, the investigators showed that much of the information content of the database was retained (3). Cells sampled from populations could still be solved, based on the values of selected latent factors, by presenting them as unknowns in relation to cells from the database (75). Thus, while the advantages of attaching quantitative values to the cells were retained, this method had the additional advantage that many or most of the latent factors used in the classification could also be interpreted in terms of qualitative shape changes, which were recognizable by the investigators on an intuitive basis.

Automation: A partial automation of the above process was achieved, in order to get rapid throughput in processing a contour or multiple contours from cells. The work that fed into automation was based on a principle of spatial mapping. Although this technique is familiar to electron microscopists, it is less commonly applied in other scientific fields. With the recent advances in methods for recognizing and extracting regions of interest from digital images, however, it became feasible to extract patterns from the electron microscope image and overlay the original image with these representations from the data. This method, called data mining, was applied to make maps of the 30-nm fiber of chromatin and thus to solve the packing order of the next higher level structures (76, 77, 78). Similar software and techniques are used to recover the boundaries from a contour or multiple contours from the image of a cell, however.

In the chromatin example, images were stored and accessed in Sun workstations, and image processing was performed with a commercial software package (Inovision Corp., Durham, N.C.) running under a SunView interface. Standard image processing routines were used. The edge details in the image were enhanced by making the first derivative of intensity in two directions. This method of processing is called "Roberts cross" in the terminology of the field and results in an image that can be thresholded. Thresholding is an operation in which minimum and maximum gray levels are established and pixel intensities falling outside these limits are set to zero. Intensity values within the threshold range are retained.

In the prior art, a series of images was made at different threshold values and these were subjected to the following data mining procedures. First, the investigators extracted patterns by employing a segmentation operation. The pattern specification in the chromatin problem was to report a pixel if it was found adjacent to any other filled pixel in the row being processed, unless the stream of coordinates reported was found to be too short or too long to represent a 30-nm structure. The program executing the algorithm ("tracit.p") reported coordinates of continuously filled structures in the image, that were on the size order of the structures we wished to segment (76, 77, 78).

A second program was designed to recognize and identify any area that might be a closed circular or elliptical figure. Working on coordinate streams output by the first program "tracit.p", the second program found the boundary on a stream of contiguous filled pixels. An algorithm executed in this program enabled a gap between unfilled pixels to be "filled in", if it were the size of two pixels or fewer. If, even after this gap-filling routine, the figure did not form a closed contour, it went unreported. The output files of vectors incorporated values of the perimeter, area, and the equation for the ellipse of concentration of the closed figure. When figures were extracted from the thresholded series, their mode areas were found to be in the interval 676–784 nm2. Since this compared favorably to the hypothetical 707 nm2 area of a 30-nm chromatin fiber in cross-section, the regions of interest were thought to consist largely of the outlines of 30-nm fibers (76). Dimensioned data on the figures from all of the thresholded images were accumulated into a file, which was processed for statistical analysis in a package of commercial software (78).

The above method has been used analytically but never to assay for cell characteristics, until the present invention.

Substituting the interference principle for acquiring the image avoids the major drawback of the acquisition of a cell image via absorbance or optical density principles, which is that colors and intensity conferred by the stain can vary due to the irreproducibility in reagents such as the compounds used to make up different lots of the stain. Moreover, these methods are directed at the analysis of cell nuclei. These methods present a simpler subject for analysis, thereby overcoming some of the difficulties of developing algorithms for relating the different cell components, when few of the principles regulating the relationship among such components are known. The drawback of such methods is that they mainly analyze a representation which is only one portion of a cell. To overcome this limitation, while still getting around the difficulty in developing algorithms for relating different cell components, the understanding of whose relationship is incomplete, it is essential to reduce the complexity of the 3D image dataset. To this end, techniques for detecting and measuring the shape of contours in a cell have been developed.

Thus, substituting a wide range of shape variables for a narrower range of variables that have been extracted from the stained in situ tissue or cytological sample confers a greater power on the method of the present invention of distinguishing transformed and nontransformed cells.

SUMMARY OF THE INVENTION

The present invention relates to a method to gather the image information at high-resolution, to compute the values of variables for shape, to combine these variables' values by calculating latent factor (or derived variable) values and finally, to call upon the comparable values in the database to classify the unknown samples. The present invention relates to a method for repetitively determining a profile of quantitative features for different cells in a sample, based on a method for collecting and analyzing information on the mass distribution in cells or portions of cells by a sequence of algorithms for data extraction, and comparing the collected information to values from a relational database. The sequence of steps comprise the following: 1) optical images of high resolution are generated from a cell, and pixels representing a cell edge or contour or repeated contours in a cell are extracted from the background of the image; 2) each such image of an edge or contour is reduced to a stream of coordinate points by selecting from among the extracted pixels those that form a line on the boundary of the contour or contours from each of the cells sampled; 3) a sequence of computer algorithms is used to determine the values of variables for shape features on boundaries from such outlined contour or such repeated contours from each cells sampled (such variables may be dimensioned or dimensionless and their values may be converted to new variables by means of combining them, for example, by latent factor extraction); 4) values for a number of cells or portions of cells that have been processed in this way are compared to a range of known values previously obtained from a reference population or populations of cells or portions of cells (such comparisons between variables' values may rely on an equation drawing a relationship among them); and, 5) determining whether the cells of the unknown and known samples show any discernable difference.

The invention provides a useful method for the discovery of drug therapies.

In one aspect, the present invention relates to a method for assaying the shape features of cells and determining whether the shape features are altered by exposure of the cells to a pharmaceutical or biological agent, comprising the steps of:
(a) culturing at least two samples of a cell population, a first treated sample population being cultured in the presence of a test agent and a second untreated sample population being cultivated in the absence of the test agent,
(b) generating a high-resolution image of each cell to be sampled from each of the sample populations as representative of the cultures, which image presents high contrast information in at least one contour of the cell or a portion of the cell,
(c) extracting at least one contour from each cell or portion of a cell sampled from each of the sample populations,
(d) extracting at least one boundary of at least one contour from each cell or portion of a cell that was sampled from each of the sample populations,
(e) determining area, perimeter, and obtaining an equation for ellipse of concentration of the cell or portion of the cell and determining at least one or more variables representing shape features of the boundary or boundaries extracted from the contour or contours of one cell or portion of one cell,
(f) repeating steps a-e for each cell sampled from each of the sample populations, and
(g) determining whether any two populations of cells sampled, with and without exposure to test agent, differed from one another by using the values of the variables.

In certain aspects, the high contrast can be introduced by imaging cells attached to a reflected light interferometer. The high contrast can be generated at the cell edge or at one or more interference contours, and the contrast can be augmented by image processing.

In certain aspects, the present invention includes a method where values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

In certain aspects, the present invention includes a method wherein at least one or more derived variables are based on different shape derived variables' values and the derived variables' values are used as a basis to compare the cells of a sample to reference values in a database.

In certain aspects, the present invention includes a method wherein, in step (g), some or all variables' or derived variables' values are used to classify the cells and determining whether the cells of the sample of the sample population differ from cells of any other sample by steps including:
(h) classifying the cells of treated and untreated sample populations by means of variables' or derived variables' values, wherein the comparison between the values from the samples is based upon reference values in a database, and such values used in a suitable classification equation including maximum likelihood estimation, multiple linear regression, and neural network, and the like,
(i) determining the value of at least one statistic describing a characteristic of at least one sample of cells, and
(j) determining that the untreated population that was sampled differs from the population treated with the pharmaceutical or biological agent, or comparing the variables' values for sampled cells against data in a database.

In certain aspects, the present invention includes a method, in which execution of the steps serves as a rapid assay for properties or characteristics of a cell significantly related to carcinogenesis or cancer.

In certain aspects, the present invention includes a method, in which execution of the steps serves as a rapid assay for an individual drug or a mixture of drugs, which drugs may reverse the cancer phenotype of cells, including:
cells derived from liver, bile duct, or gall bladder including IAR20 PC1 cells;
cells derived from respiratory airway lining including 1000 W cell line,
cells derived from other endodermal tissue origins in ontogeny including epithelial lining cells of the stomach, pancreas, intestine, urinary bladder, urethra, and thyroid gland; and,
cells derived from ectodermal tissue origins in ontogeny including epithelial lining cells of esophagus, mouth, nasopharyngeal cavities, mammary gland.

In certain aspects, the present invention includes a method, in which execution of the steps serves as a rapid assay for the chemotherapeutic or chemopreventive effect of an individual drug or a mixture of drugs inhibiting development of cancer.

In certain aspects, the present invention includes a method, in which derived variables' values used to solve for a cancer-related phenotype of a cell include at least one of FACTOR1, FACTOR2, FACTOR3, FACTOR4, FACTOR5, FACTOR7, FACTOR8, FACTOR11, FACTOR12, FACTOR13, and FACTOR16.

In certain aspects, the present invention includes a method, in which execution of the steps serves as a rapid assay for properties or characteristics of a cell significantly related to carcinogenesis or cancer.

In certain aspects, the present invention includes a method, in which execution of the steps serves as a rapid assay for the chemotherapeutic or chemopreventive effect of an individual drug or a mixture of drugs inhibiting development of cancer.

In certain aspects, the present invention includes a method for assaying shape features of cells and determining whether the shape features are altered by exposure of the cells to a pharmaceutical or biological agent, wherein one or more of the steps are executed by an instruction set encoded as a program in software in a high-speed computer, comprising the steps of:

(a) culturing at least two samples of a cell population, a first treated sample population being cultured in the presence of a test agent and a second untreated sample population being cultivated in the absence of the test agent, (b) generating a high-resolution image of each cell to be sampled from each of the sample populations as representative of the cultures, which image presents high contrast information in at least one contour of the cell or a portion of the cell, (c) extracting at least one contour from each cell or portion of a cell sampled from each of the sample populations, (d) extracting at least one boundary of at least one contour from each cell or portion of a cell that was sampled from each of the sample populations, (e) determining area, perimeter, and obtaining an equation for ellipse of concentration of the cell or portion of the cell and determining at least one or more variables representing shape features of the boundary or boundaries extracted from the contour or contours of one cell or portion of one cell, (f) repeating steps a–e for each cell sampled from each of the sample populations, and (g) determining whether any two populations of cells sampled, with and without exposure to test agent, differed from one another;

wherein one or more of the steps are executed by an instruction set encoded as a program in software in a high-speed computer, comprising:

(h) focusing of the cell or a portion of the cell at the level of at least one contour while an image is captured in a charge-coupled device or video camera and written in a recognized software format in computer memory, (i) processing a single image or a series of images of the cell or portion of the cell by at least one of a series of image processing algorithms including edge enhancement and thresholding, (j) separating pixels representing a contour or repeated contours of the cell or portion of the cell from the pixels representing background, (k) extracting a boundary on the contour or contours from among the pixels representing an image of the contour(s) of a cell or portion of a cell, (l) determining values of an equation of ellipse of concentration and at least one dimensioned variable and determining the value of at least one dimensionless shape variable reflecting shape features of at least one boundary on the cell or portion of the cell, (m) combining the values of the variables into a data set representative of at least a sampled population from the treated and untreated groups, and (n) determining whether the cells of the unknown and known samples show a significant difference.

In certain aspects, the present invention includes a method for assaying shape features of cells and determining whether the shape features are altered by exposure of the cells to a pharmaceutical or biological agent, wherein one or more of the steps are executed by an instruction set encoded as a program in software in a high-speed computer, in which execution of at least two of the steps is directed by a script to automate extraction of a boundary or boundaries from at least one contour of the cell or portion of the cell and/or the determination of at least one dimensioned and at least one dimensionless feature from the boundary or boundaries.

In certain aspects, the present invention includes a method for assaying shape features of cells and determining whether the shape features are altered by exposure of the cells to a pharmaceutical or biological agent, wherein one or more of the steps are executed by an instruction set encoded as a program in software in a high-speed computer, further including determining whether the cells of unknown and known samples show any discernable difference.

In certain aspects, the present invention includes a method for assaying shape features of cells and determining whether the shape features are altered by exposure of the cells to a pharmaceutical or biological agent, wherein one or more of the steps are executed by an instruction set encoded as a program in software in a high-speed computer, in which a program stream and lists of input files and output files, along with an optional cache for error messages, are represented by icons on a graphical user interface.

In certain aspects, the present invention includes a method for assaying shape features of cells and determining whether the shape features are altered by exposure of the cells to a pharmaceutical or biological agent, wherein one or more of the steps are executed by an instruction set encoded as a program in software in a high-speed computer, in which execution of the steps serves as a rapid assay for properties or characteristics of a cell significantly related to carcinogenesis or cancer.

DESCRIPTION OF THE FIGURES

FIG. 5 is a Table 1 showing factors (derived variables) capable of discriminating passages within a cell line and their direction of change in transformation.

FIG. 6 is a Table 2 showing factors (derived variables) used for solving transformed-type phenotypes and changes observed upon treating cells with pharmaceutical agents.

FIG. 7 is a Table 3 showing the effect of MT inhibitors and an inhibitor combination on variables that contribute to the value of factor #4 (derived variable #4).

FIG. 9 is a schematic diagram of values of variables that are relied upon in determining factor #4 (derived variable #4).

DESCRIPTION OF THE PREFERRED EMBODIMENT

Figure 1:
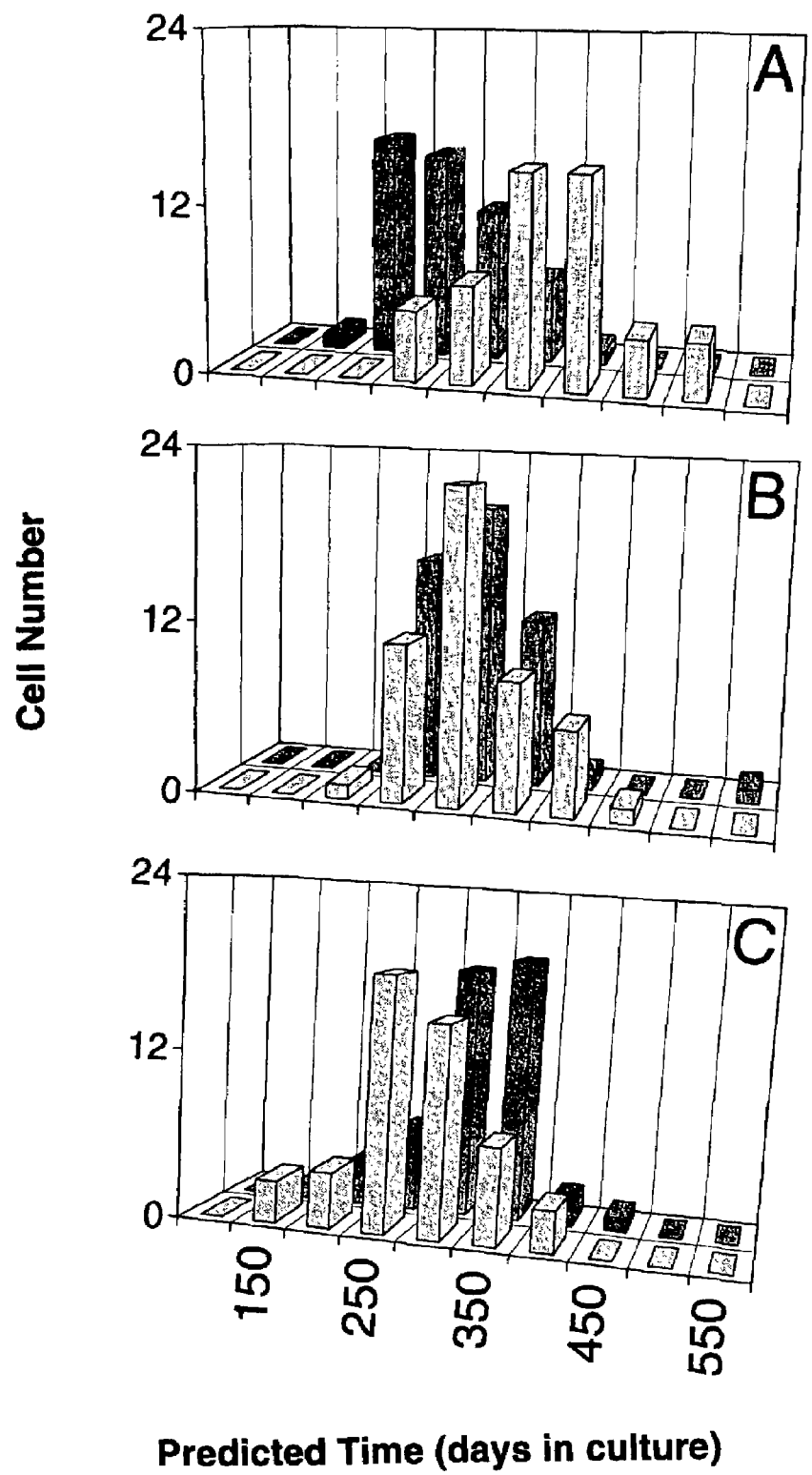
FIGS. 1A–1C are graphs showing frequency histograms showing the number of IAR20 PC1 cells classified in various categories of predicted time. Classification was based on the values of factors #1, #3–5, #7, #8, #12, and #13. The predicted time, representing a gradation of transformed types, was calculated for samples after exposure for 2 hr to: A. 0.2% solvent vehicle (back), 0.5 μM gramicidin D (front), B. 200 μM quinidine (back), 10 μM valinomycin (front), C. 2 μM colchicine (back), or 18 μM paclitaxel (front). The mean values of the colchicine- and paclitaxel-treated samples were 338 and 304 days respectively. Samples treated with quinidine ($Z_{alpha/2}$=5.66) and gramicidin D ($Z_{alpha/2}$=10.08) were significantly different from control both in this classification scheme. Previous studies based on single variables' values gave the same result. The probability of obtaining differences as large as this on the basis of random chance alone was $P \leq 0.001$. Transformed-type features of paclitaxel-treated cells, classified on the basis of variables, were indistinguishable from control ($Z_{alpha/2}$=0.32).

The present invention is an improvement on previous work by the inventor herein which led her to discover that transformation-dependent changes in cell shape are caused, in part, by a perturbation of vesicle traffic (1).

A comparison of normal and oncogenically transformed cells indicated that the latter had an excess of membrane-bound vesicles trapped in the peripheral cytoplasm. For the sake of brevity, these native differences are referred to as the signature-type of transformed cell. The signature-type could be modeled by exposing cells to one of four different classes of agents. One class was represented by a phorbol ester tumor promoter, which was thought to affect cells by activating protein kinase C (PKC). An additional class of compounds affected MTs. The remaining two classes of agents affected ion and proton transport and caused alkalinization of intracellular organelles. Work from other laboratories showed that cells treated with bioactive phorbol esters accumulated contents in the endocytic pathway to an unusual extent (2). Since the other agents also interrupted normal endosome processing, this phenotype appeared common to cells treated with all four types of agents (1). The earlier research had been done by culturing cells on interferometers and digitizing their interference contours. From the shapes of three such contours, values for a total of 102 variables were extracted, of which only a small subset was used in classifying the treated samples. These variables provided a means of categorizing each cell according to its shape characteristics, so that it could be known which agents mimicked the effects of cancerous transformation. Until the present invention, however, it was not possible to break down such transformations further into their component changes using the original classification protocol. This was a formidable obstacle to gaining a full understanding of the physiological defects of transformed cells.

In order to learn what defects were enhanced by each of the above agents, to cause mimicry of the transformed phenotype, it was essential to make qualitative as well as quantitative distinctions among cell types. It was also an essential condition to determining whether aberrant membrane processing was the major change that occurred when cells adopted the signature-type. Improvements in classification methodology are used to group like changes among the variables together and represent them by a single factor. When the original contour shape data are broken down by factors, we noted that some of the latter data corresponded to observable morphological features of cells (3). FIG. 5—Table 1 defines features described by the various factors used in classification exercises. Notable among the factors was #4, which reflected the prevalence of filopodia or microspikes, cell specializations that are induced in other model systems by activation of the G protein, Cdc42 (4–6). Thus, factor #4 values increased with the increasing frequency or length of these actin-based structures. It is possible that other factors reflected the retention of extracellular fluids in endosomal compartments. Possible candidates for such a role, for example, were those indexing the prevalence of hollowed-out regions (#13) and the variance in projection size (#11), respectively, in the second contour.

Factor-based analysis has the potential of allowing the effects reported earlier to be broken down and to distinguish subtypes among the different treatment groups, by the simple expedient of comparing factor values for treated samples and controls. It can also be determined whether there is an exact correspondence between the changes caused by agents simulating the signature-type and the bona fide transformed cell. The results show that two classes of agents, ionophores and MT inhibitors, cause a reduction in values of factor #4. The factors that might have been expected to change, however, were those related to the second contour (#11 an #13) or to bumpiness in both the uppermost contours (#2). The results of these experiments were intriguing in that they showed an underlying coordination between physiological processes and otherwise unrelated morphological features. There are several ways of making disproportionate changes in factor #4. One of them requires compensatory changes of membrane trapping in early endosomal compartments. Other compounds causing mimicry of the signature-type had more subtle effects, which did not rely on alterations in one or two specific factors.

Of the various pharmaceutical agents that were found to model the signature-type, all showed a promoter-like effect (reviewed in ref. 1). However, there was preliminary data suggest that reversal of the transformed phenotype occurred in cells treated with an MT inhibitor combination (IC) consisting of colchicine with a molar excess of paclitaxel (Heckman C A and Plummer H K III: Anticancer Res 12:1915–1916, 1992). At the time this result was obtained, little could be done to elucidate the features that were changed to create this phenotype. However, as shown by the present invention, the IC-mediated reversal is real and appears to rely upon reversal of the same effects as are promoted by treatment with PMA or weak bases. Moreover, the effects were specific to one cell line, and they were opposite in direction to the effects of paclitaxel itself on sharp, tapering features of the cell edge. The results implied that early endosomal processing occurs normally during IC-mediated reversal of the signature-type. Additional data showing MT localization were gathered by immunofluorescence techniques. These show that the sharp, tapering morphogenetic features which are notably reduced in ionophore- and colchicine-treated cells relate to MT positioning at the cell edge.

Earlier experimental results suggested that all four classes of pharmacological agents that affected the transformed phenotype interfered with endocytic vesicle processing (1). In order to see whether any of these treatments yielded an exact replica of the signature-type, it was essential to be able to compare the morphological features represented in two samples on a quantitative basis. This was made possible by a method of phenotype classification which, although based on the same contour shape variables as formerly used, enabled us to break down each cells' phenotype into new variables called latent factors (3). With the new method of the present invention, notable discrepancies between the type created by experimental treatment and the signature-type of bona fide transformed cells were found. When the morphometric patterns of the cells in experimental samples were subjected to analysis based on factor values, the outcome suggested that it was possible to interpret the four classes as affecting a few key activities. One of these was composed solely of factor #4. Others reflected additional cell edge features (#7), the arrangement of organelles in the interior of the cell (#2, #11, #13), or cell spreading (#12, #16). Since these data might provide clues as to the regulatory pathways affected by the transformation event and how they contribute to deregulated growth, a detailed analysis of the four classes of agents and their effects on physiological processes was performed.

Both dissociation of ligand-receptor complexes and ligand transfer to the lysosome can be inhibited by monensin and weak bases (19,20). Likewise, MT depolymerization interfered with the separation of ligand-receptor complexes and inhibited the transfer of proteins into late endosomes and their degradation in the lysosome (21,22). Since both monensin and colchicine reduced the prevalence of sharp projections in the shape phenotype, an interference with ligand-receptor processing was linked to this particular feature of the transformed cell. Although this effect was first reported in the current research, it is consistent with previous results showing that monensin treatment mainly affected variables of the cell edge whereas the signature-type involved changes in both of the lowermost contours (1). Since the data suggested that enhanced $Na^+$ or $K^+$ pump activity and the consequent increase in $K^+$ concentration were not responsible for cells taking on the signature-type, the outcome of the ionophore experiments appeared to rely on the piling-up of contents in endosomes.

While monensin, a $Na^+/H^+/K^+$ ionophore that carries monovalent cations across membranes in exchange for protons, causes the trapping of membrane receptors in endosomes, there is also a failure to recycle to the cell surface (reviewed in ref. 1). This trend is duplicated by the membrane as a whole, as indicated by studies from another laboratory demonstrating inhibition of fluid-phase marker uptake (23). These data suggested that a fraction of the plasma membrane became immobilized in the trapped form. It is confirmed herein that there was a reduction in the rate of uptake in the longer term. Despite the fact that the uptake of the marker, horseradish peroxidase, by IAR20 PC1 cells was not inhibited immediately after monensin treatment, it was inhibited within 30 min after initial exposure. However, marker was accumulated in larger compartments in monensin-treated IAR20 PC1 cells than in control cells (data not shown). Therefore, endocytic rates were reduced as a secondary effect of membrane trapping. Moreover, traffic in a newly synthesized pool of membrane that is ordinarily available for insertion into the plasma membrane may be impaired by a blockade of endocytosis-linked exocytosis. A mechanism that couples transport in the inward and outward pathways of MT-mediated vesicle traffic may prevent traffic in the constitutive secretory pathway (24,25).

Two additional ionophores that have a monensin-like effect on sharp projections of the cell edge were found. One of them, gramicidin, was a selective transporter of sodium and was expected to equilibrate the $Na^+$ concentration. The second, valinomycin, is selective for $K^+$ over $Na^+$ and is used to short-circuit the membrane potential (26). The fact that all three ionophores, monensin, gramicidin, and valinomycin, elicited similar cell phenotypes suggest that all of the ionophores act by elevating the pH of an intracellular compartment. Thus, in all three cases, trafficking was thought to be affected through the flux of monovalent cations into organelles. As indicated by the example discussed herein, colchicine resembles these ionophores in its qualitative effect on the factor-based phenotype. However, the mechanism employed in this case no doubt differed from that utilized by ionophores. MTs are used by cells to direct the traffic of both secretory and endocytic transport vesicles, and so their depolymerization is thought to inhibit a later step of endosome processing, namely that which mediates the separation of vesicles containing ligand only from those having ligand-receptor complexes (27). As was the case for monensin, MT-depolymerizing agents did not inhibit the instantaneous uptake of fluid-phase markers, but in cells exposed for longer times, appeared to repress endocytosis (28). Thus, the colchicine effect probably reflects the same membrane pooling process as was induced by monensin. The prevalence of sharp features in ionophore and colchicine-treated cells is reduced whenever endosomal processing is terminated at an early stage.

The defect in processing leads to a reduction of sharp, tapering projections. Although the mechanism by which the sharp features are produced is unknown, two explanations are possible consistent with the current understanding of membrane processing. One is that receptors at the plasma membrane play a role in organizing the sharp projections. If, during net membrane internalization, these receptors become pooled internally by membrane trapping, fewer sharp projections could be maintained at the cell edge. The second possible explanation is based on a current concept of coupling between the endocytic and exocytic pathways. According to this hypothesis, the process of membrane trapping would lead to a secondary reduction in the amount of membrane secreted. A reversed coupling of trafficking has been demonstrated in studies of yeast, where blockage of the early secretory pathway causes membrane trapping in the endocytic pathway (29). If actin microspikes are formed through site-directed membrane insertion at places specified by exocytosis of Golgi-derived vesicles, as is thought (30), then the features may be reduced owing to the failure of exocytosis to proceed. Since new membrane would not be available to be added at the cell edge, the fine, tapering projections would shrink and #4 values would decline.

To evaluate the above data in relation to the dynamic process of filopodia formation, it is important to gain further information on treatments that altered factor #4 values. Like other MT inhibitors, paclitaxel slowed the transport of endocytosed fluid-phase marker to the lysosome in some model systems (31) and caused the trapping of ligand-receptor complexes (32). These results suggested a membrane pooling effect similar to those caused by colchicine and monensin. In addition, investigators studying primary hepatocytes found that paclitaxel promoted a reorganization of the apical actin filament network and the extension of filopodia (31). The 1000 W cells, which showed an increased prevalence of sharp, tapering features, resembled hepatocytes in this respect. Nevertheless, the effects were not strong enough to change factor #4 values. On the other hand, paclitaxel was effective at promoting the signature-type in liver cells if delivered over a prolonged period of time. When the variables contributing to factor #4 were subjected to analysis, to explore the differences in the two cell lines, it was found that liver cells showed a shift in these variables like that observed in ionophore- or colchicine-treated cells. The same set of variables for 1000 W cells, however, changed in the opposite direction to that found in IAR20 PC1, indicating an increase in size or frequency of tapering projections. Although it is possible that cells responded to paclitaxel with increased vesicular trafficking rather than membrane pooling, it was an unlikely explanation of the data. Rather, the effect on filopodia formation may have involved a better integration of the pathways of endocytic and exocytic vesicle trafficking is 1000 W cells. Alternatively, actin may have been mobilized by partial dissolution of stress fibers, adding onto sites at the cell periphery.

Rounding-up of the cell (#12) and contractility are affected by MT inhibitors. An increase in the angle at which the cell rises from the substrate (factor #12) was among the morphometric features that characterized signature-type cells. The values of #12 were disproportionately affected by MT inhibitors, although not by ionophores. The two MT inhibitors' effects on this factor were also opposite in direction, since colchicine mimicked and paclitaxel counteracted the change seen in the original signature-type. Studies from other laboratories reveal the shift in #12 as being a probable result of Rho-mediated changes in actin architecture. Rho activation takes place through a cascade of events. The first step was activation of Rho by MT depolymerization and the second, that of Rho kinase by Rho. Finally, Rho kinase is thought to mediate the inhibition of myosin phosphatase, and thereby allow phosphorylated forms of myosin light chain kinase and/or myosin regulatory light chain to accumulate (33–35), causing components to be added to actin stress fibers and focal adhesion sites (36,37). The MT-bound Rho guanine nucleotide exchange factor, GEF-H1, which is thought to be activated upon MT-depolymerization, is a candidate initiator for these MT-dependent effects (38).

The effects of paclitaxel were opposite to those of the depolymerizing agents in other respects as well. In cultured ovarian granulosa cells, paclitaxel itself impaired the formation of stress fibers and actin was mobilized instead to the cell periphery (16). A comparable effect is found with Cdc42Hs overexpression, which causes a reduction in stress fibers along with an increase in diffuse actin (5). Such effects are attributed to the possibility that actin mobilized when stress fibers are dissolved, can contribute to features with other actin-based architectures. In an IC, paclitaxel prevented the elevation of actin stress fibers and focal adhesion sites that had otherwise been found after treatment with the depolymerizing agent alone (37,39). Thus, the results showed that an MT-bound molecule was i) responsible for Rho activation and ii) released from MTs by colchicine—a release that was prevented if paclitaxel was also present.

Stress fibers are elaborated in other model cell lines after colchicine treatment, and indeed, this agent promoted greater quantitative shifts in the signature-type than the taxanes did in the examples herein. This was consistent with the known changes in factor #12 and suggested that the state of contraction associated with elaboration of stress fibers, was associated with increasing values of #12. On the contrary, the mechanism of paclitaxel-mediated factor #12 reversal is assumed to rely, in part, upon its inhibiting or preventing the release of the postulated Rho activator. The fact that taxanes elevated surface smoothing phenotype in one cell line and not the other is difficult to explain. It may depend on diverse causes of coupling between sharp features and membrane trapping and whether this effect may be outweighed by stress fiber actin mobilization on occasion. The difference may relate to the preprogrammed state of differentiation of the cultured cells.

PMA can alter phenotype without disproportionate effects on any single factor's value. The effects of all three classes of agents discussed above appeared to be all-or-nothing in nature, i.e., each agent either promoted the signature-type or was ineffectual. PMA-stimulated cells showed more complex changes since, in this case, different factors were disproportionately affected at different times but returned to their original values after a prolonged course of PMA exposure. The time course of changes complemented the cycle of ruffling stimulation and suppression. Ruffling stimulation by phorbol esters has been observed by a number of workers using a variety of other cell types (40–42). In 1000 W tracheal cells, PMA-mediated ruffling suppression began by 10 h after the initial exposure and became severe by 15 h PMA exposure (1). Compared to its direction of change in transformation, factor #4 values underwent reversal at the 10-h interval and therefore, increased as ruffling frequency declined. A similar cycle of ruffling stimulation occurred after growth factor administration, but this activity was found to be downregulated within an hour or less (43). Depressed values of another cell edge feature, #16, appeared to reflect a decline in lamellar cytoplasm, as the cell edges retracted at the 5-h treatment interval.

Since phorbol esters act as surrogates for diacylglycerol, which is in turn the endogenous activator of PKC, the latter is implicated in the mimicry of transformed-type features. Diacylglycerol is ordinarily released when growth factor receptors stimulate the enzyme, phospholipase C, to hydrolyze its substrate, an inositol phospholipid. By activating PKC directly, the bioactive phorbol esters circumvent these initial steps of signal initiation. The subsequent steps in the signaling process are mediated by PKC substrates or by binding of the regulatory sequence of PKC to other proteins (reviewed in ref. 44). Included among the latter is PLD, an enzyme that recruits and binds activated PKC to specific sites on membranes. PKC activates this enzyme synergistically with small G proteins, RhoA and ARF, which bind PLD directly (45–47). Since PKC activation enhances the internalization of certain cell surface receptors (48), as well as markers for the extracellular medium (49,50), the data suggest that PLD accelerates membrane processing in endocytic vesicles following their release from the plasma membrane. Alterations in trafficking may be one of the ways in which PMA causes receptor downregulation and reduces the number of receptors at the cell surface (see below). PMA-induced receptor processing, however, seems to differ in some respects from processing of ligand-receptor complexes during regular signaling (51,52). This effect may relate to the fact that ligand-bound receptors with a short residence time in the endocytic pathway escape being routed to the lysosome (53,54).

PMA profoundly alters the kinetics of both membrane uptake and processing. While PMA caused contents to pile up in the endosomal compartment because of a stimulation of fluid-phase uptake, it is still unclear whether there is any change in subsequent trafficking. Other workers have shown that receptor internalization is more sustained in phorbol ester-treated cells than in untreated cells (55). In such cells, some receptors, for example, CD4, were preferentially routed to a lysosomal compartment along with the fluid-phase contents of vesicles. In lymphocytes and macrophages, both these constituents appeared to follow a PKC-mediated default pathway (56, 57). On the contrary, the T-cell receptor escaped degradation after PMA-induced receptor downregulation, although it was normally degraded when bound to its ligand (52). Indeed, some ligand-bound receptors are routinely internalized into a different compartment from that containing rapidly recycling endosomal components (58). Thus, one distinction that remains to be made in trafficking studies is whether the receptors selectively down-regulated after PMA are accommodated in a specific endocytic compartment. The exact effects of PMA on receptor processing may be related to the known translocation of the major phosphorylated protein, myristoylated alanine-rich C kinase substrate, from the plasma membrane to the lysosome in treated cells (59). The routing mechanism following PKC activation needs to be clarified in different cell types in order to relate it to mechanisms of cell shape change.

Although the changes in factor values stimulated by PMA are complex, they are related to the physiological defects that characterize transformed cells. Although most of the factor-based alterations in cell phenotype were reversed again at 10- or 15-h times, it was found that #2 adopted the signature-type value by the 10-h interval. Further, this particular factor reflects the well-known downregulation of receptor content which is known to occur in some cells. At other time intervals, statistically significant changes in signature-type occurred which were not accompanied by a change in the value of any factor used for classification, and the properties of these samples closely resembled those of the bona fide transformed cell. The mechanism by which weak bases affected the signature-type was instructive in relationship to that of ionophores that rendered the endocytic compartments permeable to ions. Comparing these agents, it was found herein that the former caused a well-balanced mimicry of the transformed cell. Both agents were postulated to elevate the pH of intracellular compartment and thus retard the loading of endocytic vesicles into MTs. Nevertheless, the effects of weak bases appears incomplete, since work from other laboratories suggests that a substantial fraction of the endocytic vesicles formed undergo retrograde transport (19,61,62). Polarized cells, in the presence of chloroquine, show more vesicle traffic than usual from the basolateral to the apical surface suggesting that the treatment also may interfere with the routing of vesicles to the lysosome (63). The known effects of weak bases indicated that endocytic vesicle trafficking continued to some extent, and in this respect, the treated cells would bear a resemblance to those treated with PMA.

Effects of simultaneous exposure to two MT inhibitors. In addition to PMA and weak bases, a combination of MT inhibitors could cause a change in signature-type without there being disproportionates changes in any factor employed in the equation for classification. The effects of the paclitaxel and colchicine combination were specific to the cell line studied, and the signature-type shift only occurred in IAR20 PC1 liver cells. Paclitaxel, a well-known chemotherapeutic agent, has diverse effects on MT physiology. It inhibits tubulin disassembly, enhances MT stability, and inhibits the binding of MT accessory proteins (64,65). In intact cells, it also inhibited the tyrosinolation of β subunit of tubulin (13). Treatment of IAR20 PC1 cells with taxanes mainly affected the combination of factors #1 and #7, but these effects are not well understood. Paclitaxel's ability to decrease the frequency of vesicle transport on MTs (66) no doubt accounted for some of its effects on the factor values. However, having fewer vesicles being transported would be expected to enhance the roughness of boundary details, especially in the second contour, whereas the changes suggested a response like that of transformed cells where surface smoothness increased. Except for a factor measuring hollowed-out regions in the second contour (#13) in cells treated with the IC containing cephalomannine, such smoothing effects were lacking in the IC-treated cells. Whereas exposure to a number of different agents caused cells to replicate or model the mass distribution of the signature-type, the combination of paclitaxel and colchicine was the only treatment that caused type reversal. It is likely that values of several factors have been changed in order to achieve a difference between experimental and control samples, but that such differences were too small to be statistically detectable.

Results of treating with cephalomannine, instead of paclitaxel, were used to compare the features that were affected differently by the two taxanes. Variables indicating smoothing of projections on the first and second contours were affected when ICs were made with taxanes other than paclitaxel. The results suggested a broadening effect on the microspike structures, although less marked than the effects induced by colchicine and ionophores. Although IC of paclitaxel and colchicine had no statistically significant effect on the values of factor #4, a study of the primary variables that contributed to factor #1 showed that some of them were changed. Thus, if the MTs functionally integrate with stable actin structures, as is commonly thought, it can be assumed that this arrangement may be affected during reversal. Other laboratories reported that paclitaxel, whether delivered alone or in an IC with a depolymerizing agent, caused rearrangement of the MT array. As long as paclitaxel was in molar excess over the depolymerizing agent, it suppressed the organizing ability of the MT-organizing center (67,68). Observations of IC-treated cells used in this research confirmed that the patterns of MT redistribution differed remarkably from those induced by paclitaxel alone. These patterns were well correlated with the reversal effect, since MTs radiated from local centers in the cytoplasm only in cells that were exposed to the IC made up with paclitaxel.

Growth factor-induced changes in signature-type. While exposure of cells to PMA short-circuited some of the initial steps of signaling, it could induce changes in receptor processing and prolong the residence time of internalized vesicles in the cytoplasm. In order to determine how this abnormal form of signaling compared to steady-state signaling in cultured cells, we altered the ambient insulin concentration in some experiments. Insulin was known to stimulate endocytic trafficking and fluid-phase endocytosis (reviewed in ref. 69). This, however, had a minimal effect on phenotype. Whereas the signature-type cells drifted upward with higher levels of hormone, the differences were not statistically significant. In order to determine whether signature-type expression could still be induced after the growth factor-driven pathway was maximized, cells were treated with colchicine. The difference between untreated and colchicine-treated cell phenotypes decreased, indicating that cells at high levels of supplementation were less responsive. The results implied that, if signaling were driven by higher and higher concentrations of insulin, a failure in the cells' responsiveness to colchicine would be seen. Thus, it is believed that the elevation of signaling has a similar ability to activate Rho as is typically induced by MT depolymerization. Whether this effect was mediated by an increased availability of guanine nucleotide exchange factors remains to be determined. Downstream of insulin signaling, a novel isoform of PKC was implicated in the stimulation of gene transcription (70). It is believed that long-term insulin supplementation up-regulates Rho activity but that the effect was counteracted by another regulatory mechanism, possibility working at the transcriptional level. This would account for the fact that insulin supplementation failed to induce a significant change in the signature-type.

The following examples are provided merely to further illustrate the present invention. The scope of the invention shall not be construed as merely consisting of the following examples.

EXAMPLE I

Cell lines and interference preparations. Equations were developed to define changes in the signature-type for two epithelial cell lines that underwent transformation over a prolonged time of in vivo culture. Although a different equation was developed in each case, there was considerable overlap in the factors employed as variables (3). IAR20 PC1 was a clonal derivative of a line called IAR20, which was cultured from liver cells of a BD-VI rat. The other line, 1000 W, was generated from the tracheal epithelium of a Fisher 344 rat after topical treatment with 7,12-dimethylbenz(a) anthracene. The lines become tumorigenic after 11 and 16 months of being maintained in culture, respectively (3). Liver cells were grown in William's E medium supplemented with 10% fetal bovine serum, whereas the tracheal cells were grown in Waymouth's medium containing fetal bovine serum plus 0.1 μg/ml insulin and 0.1 μg/ml hydrocortisone. The cells were maintained and subcultured as described elsewhere (1,3). For experiments with insulin supplementation, insulin concentrations were raised to 1 and 10 μg/ml and maintained for two passages before the cells were used.

Information about shape features was derived from interference images. These were generated by culturing cells on anodized tantalum substrates, and then imaging them in reflected light. Cells were plated on substrates in replicate dishes, left overnight, and then exposed to experimental agents or to the solvent vehicle alone. After incubation with the agents for 2–5 h, samples were recovered, fixed in buffered 3% glutaraldehyde (pH 7.3), and air-dried. Randomly selected cells were imaged in a Zeiss Universal microscope, and the outlines of their three lowermost interference contours were digitized. A database of 102 variables for contour shape was obtained for each cell, representing its mass distribution. Each experimental treatment was represented by a total of 50 cells.

Classification procedures. The classification methods employed a subset of the contour shape variables. Each 50-cell sample was submitted to multiple linear regression analysis for classification alongside a group of cells representing normal and transformed reference samples. The latter were obtained from the lines that underwent transformation as described above. Because the signature-type value was assigned relative to these samples, the solutions were in units of predicted time in culture. After obtaining such a value for each cell in an experiment, the differences in mean predicted times for treated and control cells were calculated. The sum of the squared standard deviations, divided by the number of observations, n, was used to compute the confidence limits of the mean:

$$(s_1)^2/n + (s_2)^2/n$$

Where s was the standard deviation for each sample. Dividing the difference between the means by the square root of the above expression yields a value that can be related to the degree of confidence, 1-α. For example, a $Z_{alpha/2}$ exceeding 2.33 would indicate a large difference between the confidence limits of the mean for experimental and control samples. This value was equivalent to a probability that the two samples differed of $P \leq 0.02$.

Again, classification of samples from experiments employed multiple linear regression methods, based on factors scores rather than on contour shape variables. Factors were generated by combining into a single database, the contour shape variables from highly malignant epithelial cells and precancerous lines that change progressively, eventually become neoplastic. The database contained values of 102 variables for 200 cells each from four cell lines, thus ensuring that values of the factors reflected a wide variety of shape phenotypes. Principal components were extracted and transformed by a pattern of rotation to produce latent factors, which described variances that had thereby been rendered orthogonal (8). Factor scores for each cell represented in the database to be estimated. These factor scores from known IAR20 PC1 or 1000 W cells are used as a reference to classify data from short-term experiments on the respective samples. The factors used in classification were selected by the SAS REG procedure (8). Equations describing the relationship among factors were unique to each line (3,7). Predicted time-in-culture values were obtained by submitting the experimental cells to analysis, as described above for simple variables. The statistical significance of differences among sample means within each experiment was determined by the Duncan multiple range test. To determine whether any factor's values differed among treatment groups within an experiment, the GLM and MODEL discriminant analysis procedures of SAS were used. Factor scores for dependency on the transformed state of each line by computing Pearson's product-moment correlation with time, using S-Plus software (Statistical Sciences, Inc, Seattle, Wash.) were also tested.

In further evaluating the factors used in the classification equations, a few of the factors were entered into the equations by multiple linear regression selection but were not well correlated with transformation. Presumably, these were entered because they counterbalanced fluctuations in the value of one or more factors that were well correlated with transformation. Examples of this effect include factor #1, which indexed massive protrusions or eroded features in the upper contours. These features became less prevalent in the signature-type of IAR20 PC1 cell but showed no correlation with time in the 1000 W line. Another example was the factor for variance in size of features in the second contour, #11, which was used in classifying cells from the tracheal line. As it defined features that were changed in the signature-type of 1000 W, along with factor #2, which described the number and size of projections and invaginations in the uppermost contours, it was thought to counterbalance fluctuations in the values of #2. A similar effect was noted with #8, a factor for sharp features in the second contour, which was included in the classification equation for IAR20 PC1 cells, although it showed no significant correlation with transformation in this line.

Chemicals. Quinidine sulfate, gramicidin D, valinomycin, monensin, ouabain, and colchicine were obtained from Sigma-Aldrich Company (St. Louis, Mo.) and used as previously described (1). Cells were exposed to these agents at concentrations indicated in the text. All stock agents were dissolved in ethanol and stored at −20° C. Baccatin III, cephalomannine, and paclitaxel were gifts from N. R. Lomax and M. Suffness, Drug Synthesis and Chemistry Branch and Natural Products Branch, respectively, of the Developmental Therapeutics Program, Division of Cancer Treatment, National Cancer Institute. PMA and 7-deoxytaxol were obtained from LC Laboratories (Woburn, Mass.). Cells were exposed to baccatin III at a concentration of 9 μM, whereas the other taxanes were used at concentrations of 6–18 μM. No concentration-dependent differences were observed within this range.

Immunofluorescene localization of β-tubulin. IAR20 PC1 cells were subcultured onto sterile glass cover slips as described above. Replicate samples were exposed to test agents for 2–5 h alongside controls, and then fixed and left in methanol at −70° C. until used for the immunofluorescence procedure. To visualize arrays of MTs, cells were exposed to a mouse monoclonal anti-β tubulin antibody (Nycomed Amersham, Little Chalfont, Buckinghamshire, UK), made up at a 1:300 dilution. We used a 1:100 dilution of P3×63 monoclonal antibody from P3 myeloma (generous gift from J. Lessard) as a non-specific control. The secondary antibody, EITC-conjugated goat anti-mouse immunoglobulin G (US Biochemical Corp., Cleveland), was used at a dilution of 1:2000. Cover slips were processed and then mounted on a slide in a solution of 1,4-diazobicyclo[2.2.2]octane (Sigma) made up to 25 mg/ml in glycerol. The samples were photographed on a Zeiss Axiophot microscope equipped with a 63x Planapo lens. Images were recorded on Kodak Tri-X or T-Max film. All of the drugs, including paclitaxel, cephalomannine, colchicine, and baccatin III, were studied to see if they affected the arrangement of MTs. Except for a tendency to develop more prominent bundles with time, no structural differences were noted in cells depending on the duration of exposure to the taxanes. MT arrangement was unaltered after treatment with the above-mentioned ionophores and transport inhibitors. Immunofluorescent staining in cells treated with non-specific control immunoglobulin was negligible and failed to localize on any cytoskeletal structures.

Results: Since some of the features changed in transformed cells were represented by discrete factors, each experimental treatment was broken down by factor values and it was determined whether each pattern of mimicry was attributable to a specific factor. Using data collected from a progressive series of PMA-exposure intervals on 1000 W cells, it was found that the signature-type was maximally expressed at 5 h and then underwent gradual reversal so that, by 10 h after treatment, the samples were classified as normal again. The results were similar to those reported earlier based on classification by values of single variables (9). In the factor-based classification, predicted times were 612, 648, 663, 668, and 604 days, respectively, for samples collected at times zero, 30 min, 2 h, 5 h, and 10 h after exposure. Accumulation of fluid-phase contents was also enhanced over a similar time interval (1).

To determine whether this time course involved changes in specific morphological components, the values of those factors that were relied upon most heavily to identify the signature-type were analyzed. Factor #1 was significantly elevated for a brief period after exposure, but reverted to control values within 2 h (data not shown). Factor #2 values were significantly reduced below control at the 10-h time point. Other strong predictors of the signature-type, including #4 and #12, showed values that were indistinguishable from those of control samples at times between 0.5 and 5 h. In one experiment, some factors were altered over the control, but they were those that accounted for relatively little of the original change in signature features. Both #7, an indicator of knob-shaped projections on the cell edge, and another weak predictor, #16, an index of the size variability in projections at the cell edge, adopted values like those of transformed cells. In a second experiment, none of the factors relied upon for classification showed a significant difference from the control values at the 5-h time of phenotype expression (Table 2).

Ionopores and colchicines reduce the frequency of sharp projections. Certain agents that alter the content of intracellular ions and protons cause fluid-phase contents to accumulate in cells by blocking traffic in the endocytic pathway. Monensin is the agent that has been most widely used to study such effects. The phenotypes that were produced in cells by treatment with monensin, gramicidin, and valinomycin, were compared to determine whether they were qualitatively similar. Monensin, which had been found to enhance the signature-type in early work, equilibrated both protons and monovalent ions across the membrane. Gramicidin had equal affinities for $Na^+$ and $K^+$ but resembled monensin in that it allowed intracellular levels of $Na^+$ to rise (10). Valinomycin predominantly bound and transported $K^+$ and was used to induce energy-dependent $H^+$ ejection from organelles (11). With factor-based analysis, both valinomycin and gramicidin D shifted the phenotype of IAR20 PC1 liver cells to values of 336 and 387 days, respectively, compared to 283 days for control (FIG. 1). When the values of the individual factors used for classification were analyzed, the following differences were found. A high concentration of monensin used in previous studies (1) was found to cause substantial changes in several factors. A change in factor #4 was common to these cells (data not shown), however, and to those treated with gramicidin and valinomycin (FIG. 6—Table II). The value of #8 was also affected by valinomycin treatment in one experiment shown in Table II, as well as by exposures of 24 μM monensin (data not shown). Gramicidin was unique among the ionophores in that it caused an increase in factor #7 values, indicating a greater prevalence of knob-like structures at the cell edge.

The above results show that the exact composition of the monovalent ion transported was irrelevant to signature-type induction. An additional anticipated outcome after monensin exposure, at least, was membrane hyperpolarization which could be expected to result from stimulation of plasma membrane $Na^+$, $K^+$ pump activity. The possibility that this was instrumental in signature-type mimicry was ruled out by administering monensin along with ouabain. The latter blocked monensin-induced acceleration of $^{86}Rb^+$ entry in other model systems (12) and thus prevented hyperpolarization. When cells were exposed to 24 μM monensin alone and classified on the basis of factor values, their average predicted time was solved as 344 days, compared to 318 days for the control. Administration of monensin together with 50 μM ouabain caused the phenotype to shift to 347 days, a value that differed significantly from control (data not shown). The results indicate that blocking the $K^+$ binding site has no effect and therefore, that stimulation of $Na^+$, $K^+$ pump activity is not essential for the expression of the signature-type.

Colchicine is as potent as monensin at inducing the signature-type. Under conditions employed in our experiments, colchicines caused the complete depolymerization of MTs. Thus, the effect is attributed to the fact that MT integrity was crucial for the normal processing of endosomal contents. When IAR20 PC1 cells were treated with colchicine and then classified by factors, the equation solution advanced to 338 days in culture, over the 283 days obtained for control (FIG. 1). Qualitatively, as well, the colchicine-induced phenotype resembled that induced by ionophores. The prevalence of filopodia (#4) decreased, as had been observed in ionophore-treated cells. In one experiment, the factor #7 value increased for the colchicines-treated sample indicating that knob-like structures at the cell edge were affected, as had been found in gramicidin-treated cells (FIG. 6—Table 2). The arrangement of MTs was unaffected by ionophore exposure (data not shown), and so the general similarities in phenotype did not imply that a common mechanism mediated the cell's response to the two classes of agents. Two major differences were seen in the response, one in values of #12, a factor that reflects the slope at which the cell surface rises from the substratum. Both factor #12 and, in 1000 W cells, #1, a factor for massive extensions or invaginations in the two uppermost contours, increased in cells exposed to colchicine but not in those exposed to ionophores.

The effect of MT-stabilizing drugs, such as paclitaxel, was also studied. Paclitaxel caused bundling of MTs, so that they were gradually excluded from the rest of the cytoplasm. In some cells types, it inhibited MT-dependent traffic of endosomes to the lysosome (13), whereas in others, internalized receptors were degraded at the normal rate in the presence of the taxane (14). Paclitaxel impairs the movement of lysosomes along MTs although to a lesser extent than MT-depolymerizing agents (15). The data suggest that the effects on endosome processing were cell-type specific and that paclitaxel might stimulate features of the signature-type in some cells. Indeed, preliminary results show that the agent has this effect on IAR20 PC1 cells, if it was administered at a high concentration over a 4-h period (Heckman C A, J Cell Biol 111: abs. 52, 1990). When this phenotype is broken down in terms of factors, the cells exhibited changes in #1, #7, #8, and #13 (data not shown). Differences seen in factors #1, #7, and #13 were not unique to paclitaxel, since similar effects were obtained with at least one sample exposed to another taxane. Exposing the cells to a lower dose of paclitaxel for 2 h led to changes in factors #1, #7, and #12, and the values of the former two came to resemble those of transformed cells (FIG. 6—Table 2). Nevertheless, the treatment failed to promote the signature-type of these cells, as the solution for mean value of predicted time was 304 days, compared to 283 for control (FIG. 1), a difference that was not statistically significant. Similarly, no difference was found when the data were classified on the basis of single variables.

Weak based induce the signature-type without significant changes in any factor value. Cells were exposed to the antimalarial drugs, chloroquine and quinidine sulfate, and solved for values of predicted time in culture. Values of 315 and 332 days, respectively were found. These differed significantly from the control value of 283 days (FIG. 1). Although quinidine had not been tested previously, a similar result had been obtained for chloroquine when classification was based on single variables (1). Since weak bases freely enter and neutralize acidic compartments, the results confirmed the importance of proton concentration and pH in causing cells to adopt the signature-type. When samples treated with the weak bases were analyzed for significant changes in factor values, it was found that these compounds did not significantly change any of the factors used in classification (FIG. 6—Table II).

Figure 2:
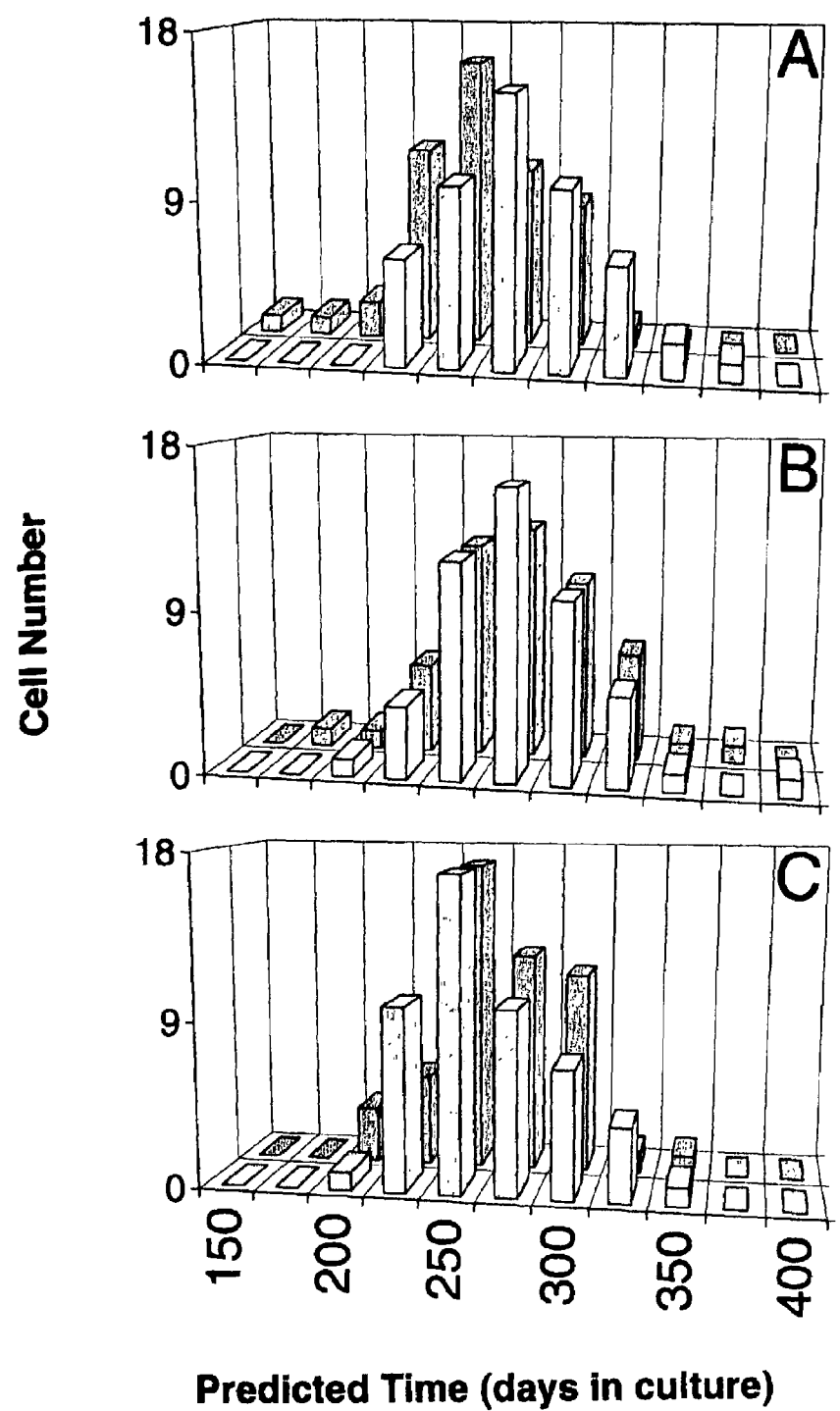
FIGS. 2A–2C are graphs showing frequency histograms showing the number of IAR20 PC1 cells classified in various categories of predicted time. Classification was based on the values of factors #1, #3–5, #7, #8, #12, and #13. The predicted time, representing a gradation of transformed types, was calculated for samples after exposure for 2 hr to: A. 18 μM paclitaxel plus colchicine (back), 0.2% solvent vehicle (front), B. 18 μM cephalomannine plus colchicine (back), 6 μM cephalomannine (front), C. 18 μM 7-deoxytaxol plus colchicine (back), 18 μM 7-deoxytaxol (front). The final concentration of colchicine was 2 μM. When classification was based on single variables' values, samples treated with cephalomannine alone ($Z_{alpha/2}$=0.82) and deoxytaxol plus colchicine ($Z_{alpha/2}$=1.07) were indistinguishable from control. On the contrary, cephalomannine plus colchicine ($Z_{alpha/2}$=2.42) and deoxytaxol ($Z_{alpha/2}$=2.38) appeared different from control. The probability of obtaining differences as large as these on the basis of random chance alone was $P \leq 0.03$.

Phenotype reversal upon exposure to a combination of MT inhibitors (IC). Certain taxanes, when administered simultaneously with an MT inhibitor, stabilized the MTs against depolymerization. It was reasoned that, if the colchicines-induced shift to the signature-type required MT depolymerization, then treatment with an IC containing such a taxane would counteract the response to colchicine and maintain the normal type. To explore this possibility, IAR 20 PC1 cells were to a combination of paclitaxel and colchicine. The results were unexpected, however, as the IC treatment reversed the signature-type pattern. The mean predicted time for the treatment sample was 265 days, versus 291 days for the control (FIG. 2) to determine whether this effect could be achieved by delivering colchicine together with a paclitaxel analogue, two such analogues and their ICs were studied. However, the IC used initially was uniquely effective compared to those made up with other taxanes. Exposure to baccatin III, cephalomannine, or 7-deoxytaxol alone failed to shift the samples' means to values that differed significantly from control. Cells exposed to an IC made up with either of the latter two taxanes also failed to change their phenotype (FIG. 2). When values of individual factors were analyzed, both the taxane- and IC-treated samples were distinguished from the control by a difference in factor #1 value. Although there were few significant changes in cells treated with cephalomannine and colchicine, the IC containing 7-deoxytaxol caused alterations in values of several factors (data not shown). In cells exposed to the former IC, #13 underwent a shift to the value observed in transformed cells (FIG. 6—Table 2). This shift, which would have been expected to enhance the signature-type, did not lead to the sample differing significantly from control (FIG. 2). At the other extreme, cells treated with an IC of paclitaxel and colchicines could reverse their phenotype without exhibiting a significant change in any factor's value (FIG. 6—Table 2). This suggested that small shifts in a number of factors must have occurred to account for the overall shift in classification.

To investigate the reversal of the signature-type further, it was determined whether reversal could be induced by exposing 1000 W tracheal cells to paclitaxel and colchicine. The predicted time values of the samples were shifted only slightly compared to control. The signature-type of cells treated with this IC was 611 days compared to 638 days for control, a difference that was not statistically significant. When individual factors of the subset used for classification were analyzed, to determine whether their values were disproportionately affected, no significant differences were found. Even when paclitaxel was used alone, it failed to elicit any change in the signature-type of 1000 W cells. This was true regardless of whether cells were exposed for the standard 2-h interval or the exposure was lengthened to 5 h. Thus, the data suggest that reversal of the phenotype by this IC was specific to IAR20 PC1 cells. In further analyses, key variables contributing to #4, the factor accounting for the major fraction of transformation-dependent variability in the data, were investigated. It was reasoned that, if factor #4 underwent a marginal change in value, underlying changes in one or more of the eight contour shape variables that were highly correlated with it would be found. Indeed, six of their values differed significantly in paclitaxel-treated 1000 W cells, indicating that the boundary of the cell became more complex. Four of the six were still changed in IC-treated cells, suggesting that these samples differed very little from those treated with paclitaxel alone (FIG. 7—Table 3).

Use of method to find therapies and examples of diseases useful with method of invention. The effects of taxanes on 1000 W cells were dissimilar to those found when the IAR20 PC1 liver cell line was used (deposited with the ATCC under Patent Deposit Designation No. PTA-4019 on Jan. 30, 2002 and found to be viable). This cell line was taken from a deposit maintained by Bowling Green State University, Department of Biological Sciences, Bowling Green, Ohio, since prior to the filing date of the provisional application 60/280,053. Paclitaxel alone was capable of reversing the direction of change of six out of the eight above variables, compared to the direction they were shifted in transformation. These shifts in phenotype suggested that paclitaxel itself could reverse evidences of cancerous transformation. Since the IC of paclitaxel and colchicine had similar effects to those of paclitaxel alone, the data show that this taxane, alone or in combination with colchicine, had the power to reverse certain features of the cancer cells. This was not the case for IAR20 PC1 cells (FIG. 7). In these cells, the direction of change of one of the variables, CSQD, was reversed in the IC-treated cells, moving in the opposite direction to that taken after treatment with the taxane alone. Taxane treatment tended to smooth out the sharp features at the cell edge, whereas the IC enhanced the length and sharpness of such features. ICs made up with taxanes other than paclitaxel, however, had a tendency to simplify the boundaries and therefore, these ICs were totally unlike the IC containing paclitaxel.

The importance of the differences described above can hardly be overestimated, because there is a novel principle reflected by the activity of an IC such as paclitaxel and vinorelbine, another MT-depolymerizing agent. In the case of many standard chemotherapeutic drugs, they are thought to merely act as poison to the cells. The MT-inhibitory drugs are a little bit more specific than most, as they target specifically the dividing cells of the patient's body, working by poisoning the mitotic apparatus, which is used by the cell to complete distribution of its chromosomes to two daughter cells. The ICs composed of MT-inhibitors, however, are working on a more sophisticated biological level. These combination agents work by inducing the process of apoptosis (84). Apoptosis is a natural pathway of cell death, that is used normally in tissue reconstruction in order to clear away cells and tissues that are extraneous to further development of a fetus, new-born, or young animal. Since the principle of triggering apoptosis by administering the IC to the colon cancer cells is wholly unknown, it is important to have an assay whereby a biological effect of the IC may be predicted. The present invention provides an assay which predicts the biological efficacy of an MT-inhibitor combination through a means that does not rely upon mitotic arrest.

Although the two cell lines used in the above-mentioned examples are from dissimilar organs and tissues of the body, they originate from the same tissue in embryonic development. Along with the respiratory tract and liver, represented by the 1000 W and IAR20 PC1 lines respectively, other organs derived from the endodermal layer include gall bladder, pancreas, colon, small intestine, urinary bladder, urethra, and thyroid gland. Cancer cells from the epithelium of all these organs may be reversed in some of their properties when treated with taxanes. The above data provide evidence, however, that different cells from the same embryonic lineage respond very differently to paclitaxel (see FIG. 7). Thus, it is possible that taxanes as sole agents and/or combinations of different MT-depolymerizing agents with taxanes may be effective chemotherapeutic agents for some of these organ and tissue types. Evidence from medical studies on breast cancer patients suggests that an IC made up from vinblastine (Vinorelbine®) and a paclitaxel analogue, docetaxel (Taxotere®)), is an effective therapy for women who develop metastatic disease. Prospective, randomized trials have now been done with this IC, and it has been found active (85). Because of a necessity to test therapeutic treatments on patients with no known alternative that is more effective, the only data that exist to date are on patients with advanced disease. Phase I data suggest that the IC used clinically, vinblastine and paclitaxel, is effective in patients with esophageal and lung cancer, as well as breast cancer (86). Clinical tests of IC therapy as a primary treatment for breast cancer are now underway. The use of two MT inhibitors as a therapy is, therefore, in the process of being evaluated. Since the breast tissue is derived from the embryonic layer known as ectoderm, the current developments suggest that use of taxanes in an IC are effective for tissues and cells arising from both endodermal and the ectodermal lineages. There is no experimental work which can be used as a basis on which to judge whether tissue from the third embryonic lineage, called mesoderm, are also susceptible to IC-induced reversal.

It should be noted that these neoplasias were relatively differentiated in comparison to the IAR20 PC1 cells, which formed anaplastic tumors when injected into host animals. The question whether the reversal of the cells' response to paclitaxel, when it was administered in the presence of colchicine, was an important indicator of the therapeutic effect of an IC was explored. The research was conducted by clinical practitioners working on human subjects with advanced cancer.

Differences in MT organization. In order to compare the cytoskeletal organization of cells treated with taxanes alone and those treated with an IC, exposed cells to the MT inhibitor(s) and then localized tubulin. Baccatin III had little noticeable effect, but the other taxanes elicited dramatic changes in MT organization.

Figure 3:
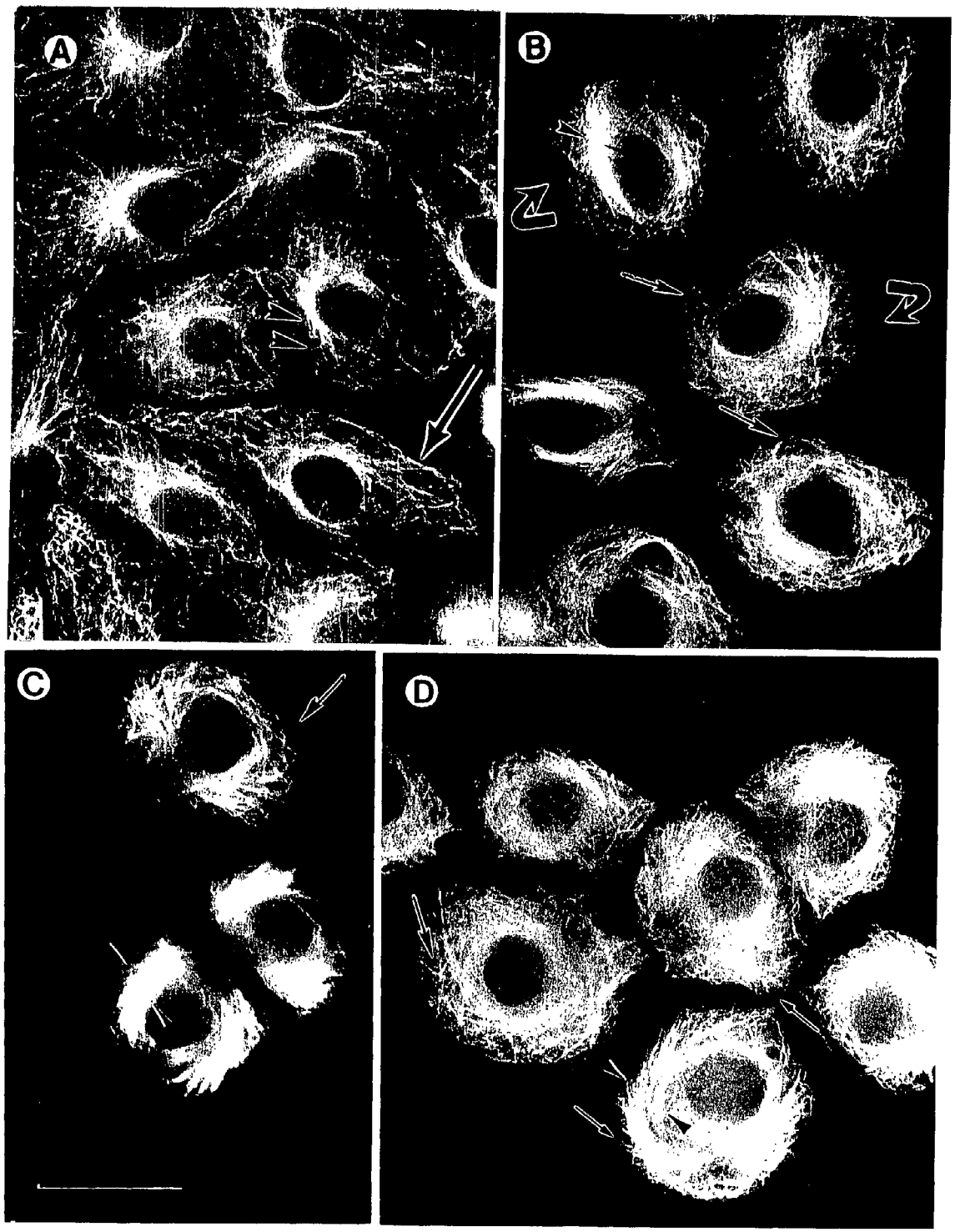
FIGS. 3A–3D are photographs showing indirect immunofluorescence staining for beta-tubulin, showing the organization of microtubules (MTs). Prior to staining, cells were treated with: A. 0.2% ethanol, B. 18 μM cephalomannine plus 2 μM colchicine, C. 18 μM cephalomannine alone, or D. 12 μM paclitaxel plus 2 μM colchicine. In control cells, MTs radiate away from the MT organizing center toward the cell edge (pair of arrowheads). Some MTs also appear to be organized at the edge itself (large arrow). Bundles of parallel MTs (opposing arrowheads) are prominent in all samples that were exposed to taxanes. Cells treated with an IC of cephalomannine and colchicine exhibit wavy MTs (straight arrows) and MTs that reach the cell edge but appear to turn back, forming a scalloped border (curved arrows). Cells treated with cephalomannine alone also show looping MTs (arrow) and bundles (paired arrowheads). After treatment with both paclitaxel and colchicine, cells have MT arrays that radiate away from points in the cytoplasm (medium arrow). These MTs are abnormally straight and often end in fringe-like arrays at the cell edge (small arrows).

Cephalomannine caused MTs to aggregate in the form of arc-shaped bundles that partially encircled the nucleus (FIG. 3). Paclitaxel-treated cells also contained large bundles of MTs, as noted by others (16,17). In both cases, changes caused by the IC were more moderate. Cells exposed to an IC containing cephalomannine appeared flatter, with more diffusely distributed MTs, than those treated with cephalomannine alone. Both samples, however, exhibited curving MTs throughout the cytoplasm and at their edges. When cells were treated with an IC containing paclitaxel, bundles were less prominent and the exaggerated MTs looked straighter and more delicate, but the bundles of MTs themselves were organized similarly to those in paclitaxel-treated cells. In nearly every cell, an area could be detected where MTs appeared to radiate away from a point in the cytoplasm. Often, more than one of these areas was present so that MTs formed a criss-crossed array in the cell periphery. Originating from such points, the areas often radiated all the way out to the cell edge (FIG. 3). Since cells treated with paclitaxel alone frequently had a fringe of straight MTs extending out toward the cell edge but lacked criss-crossed arrays, these appeared unique to the IC-treated cells. Varying the concentration of the paclitaxel in the IC between 6 and 18 μM did not change the MT organization compared to the example shown in FIG. 3.

The data show that colchicine had a striking effect on the arrangement of MTs when it was in an IC with paclitaxel, but failed to substantially alter their arrangement when it was delivered together with cephalomannine. To determine whether there was any difference in the sites where MT bundles formed after the two types of IC-treatment, the location of the bundles were tabulated. They were found on both sides of the nucleus in 71% and 56% of cells treated with cephalomannine and paclitaxel alone, respectively. The comparable values for IC-treated cells were 59% and 62%, suggesting that there was a tendency for MTs to aggregate around more than one MT-organizing center in the presence of either taxane. Control cells had a concentration of MTs on one side of the nucleus, where they appeared to converge at the MT-organizing center. Over 70% of the control cells exhibited this arrangement, while the remainder showed two sites where the MTs were convergent. This is consistent with the belief that net recruitment of tubulin into MTs and bundling of the MTs occurred, regardless of which IC was administered. In cells treated with paclitaxel and colchicine, about one-third fewer MTs appeared to radiate from the MT-organizing center than in either paclitaxel-treated or control cells. Therefore, it is believed that the suppression of MT-organizing centers around the nucleus is a distinct feature of IC-treated cells.

Figure 4:
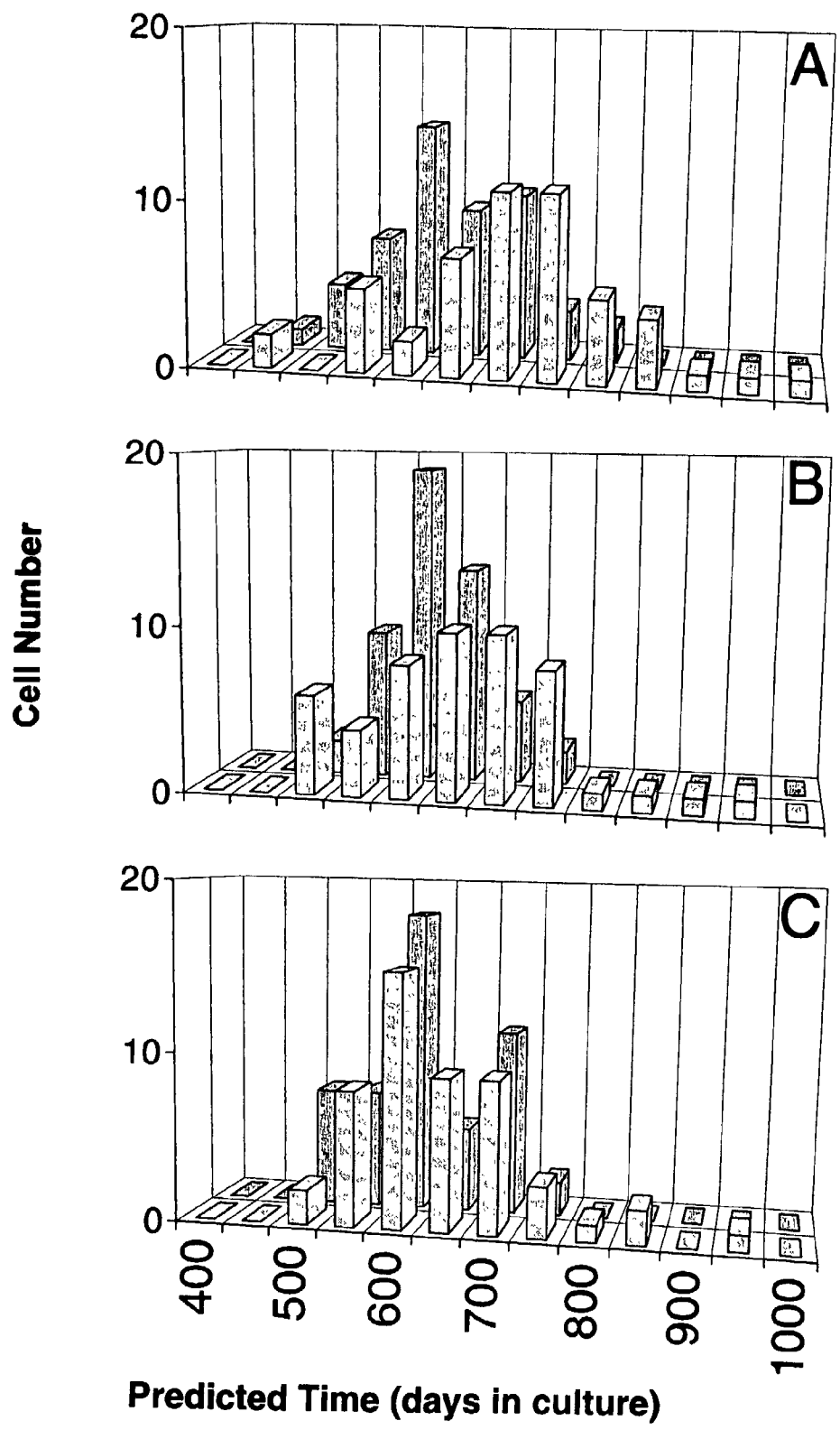
FIGS. 4A–4C are graphs showing frequency histograms showing the number of 1000 W cells classified in various categories of predicted time. Classification was based on the values of factors #1, #2, #4, #7, #11, #12, and #16. The predicted time, representing a gradation of transformed types, was calculated for samples grown in insulin concentrations of: A. 0.1 μg/ml, B. 1 μg/ml, or C. 10 μg/ml. Samples were collected with (front) or without (back) having been exposed to 2 μM colchicine for 2 hrs. The mean values for untreated samples were 655, 638, and 637 days, respectively. Comparable mean values for the colchicine-treated samples (737, 687, and 673 days) trended downward. This showed that supplementation decreased the magnitude of differences between treated and untreated samples.

Relationship of growth factor signaling to the signature-type. In other cultured model systems, insulin stimulated the rate of fluid-phase endocytosis (18). Therefore, the ambient concentration of insulin was varied to see whether this would perturb endocytic processing and hence, change the phenotype of 1000 W cells. The growth medium used for these cells contained supra-physiological levels of insulin, as it was routinely supplemented with 0.1 μg/ml insulin (approximately 10 nM). In the range about 1 nM, insulin affects cells through its ability to bind to insulin-like growth factor receptors. To determine whether shape features were perturbed by elevated signaling, cultures were grown separately in media containing three different levels of insulin. When the values of mean predicted time were solved, there were no significant differences among samples grown at levels between 0.1 and 10 μg/ml (FIG. 4). When cells cultured in replicate dishes were given a short-term exposure to colchicine, the signature-type was still created regardless of supplementation level. However, samples supplemented with the lowest level of insulin showed the most significant difference in the Duncan multiple range test. In a second experiment, the average solution of a colchicine-treated sample was 689 days, versus 636 for the control (data not shown). Two samples derived from a culture with 1 μg/ml level of supplementation still showed values of 687 and 638 days in culture respectively (FIG. 4). These samples also differed at $P \leq 0.05$, as did cells supplemented with 10 μg/ml levels. The probability of finding a value this large, based on random error alone, was $P \leq 0.001$. The value of the difference between to treated and controls was evaluated by the $Z_{alpha/2}$ value, which was 4.23 in the first pair of samples. The corresponding values for cells cultured in medium and high insulin concentrations were $Z_{alpha/2}=2.97$ ($P \leq 0.003$) and 2.22 ($P \leq 0.03$). Thus, the significance of the difference between treated and control groups declined as the insulin concentration increased.

EXAMPLE II

The mechanism of action of the tumor promoter depends on its ability to substitute for an endogenous second messenger, diacylglycerol, and thereby activate certain members of an enzyme family known as protein kinase C. The quantitative shape phenotype of cells treated with PMA resembled the phenotype of bona fide cancer cells. The effect of PMA on this phenotype was transient as explained above. When the shape phenotype was dissected into components by relating different variable's values to shape features, several of the altered values appeared to rely upon a declining number of sharp features, such as filopodia and microspikes, at the cell edge.

Filopodia and microspikes are in turn regulated by a GTPase (79, 80) of the Rho family, Cdc42, which modulates actin architecture. Although data suggest that PMA counteracts the rearrangement of actin into filopodia and microspikes, there is no known link of Cdc42 to any PMA-responsive isozyme of protein kinase C. Further, over expression of an active mutant of Cdc42 itself did not restore the phenotype to that of a normal cell (data not shown). However, Cdc42's contribution to biological effects, such as neuronal growth cone development, is antagonized by activating another GTPase, Rho itself (81). A third GTPase of the Rho family, Rac, which regulates ruffling, is likewise antagonized by Rho activation. Additionally, p21-activated kinase (PAK) mediates the effects of Cdc42 and Rac on actin architecture and promotes formation of filopodia and focal contacts, while antagonizing Rho function (82). This led to further investigation whether overexpression of PAK or inhibition of Rho activity would enhance the formation of sharp features. 1000 W cells from respiratory tract epithelium were cultured in slide chambers containing fiduciary marks and the PAK gene was injected along with a gene for green fluorescent protein (GFP). The shape phenotype was analyzed in cells that were first prepared for scanning electron microscopy and then relocated in the field of view at low magnification. To explore where elimination of RhoA activity might enhance the process of filopodia or microspike formation, a dominant negative mutant RhoA (dnRho) along with GFP was introduced. This genetic construct could inhibit Rho-mediated effects by competing for the guanine nucleotide exchange factor(s) that activates endogenous Rho. Therefore, the results obtained by overexpressing dnRho were expected to resemble those obtained when overexpressing the GTPases, Cdc42 or Rac.

Figure 8:
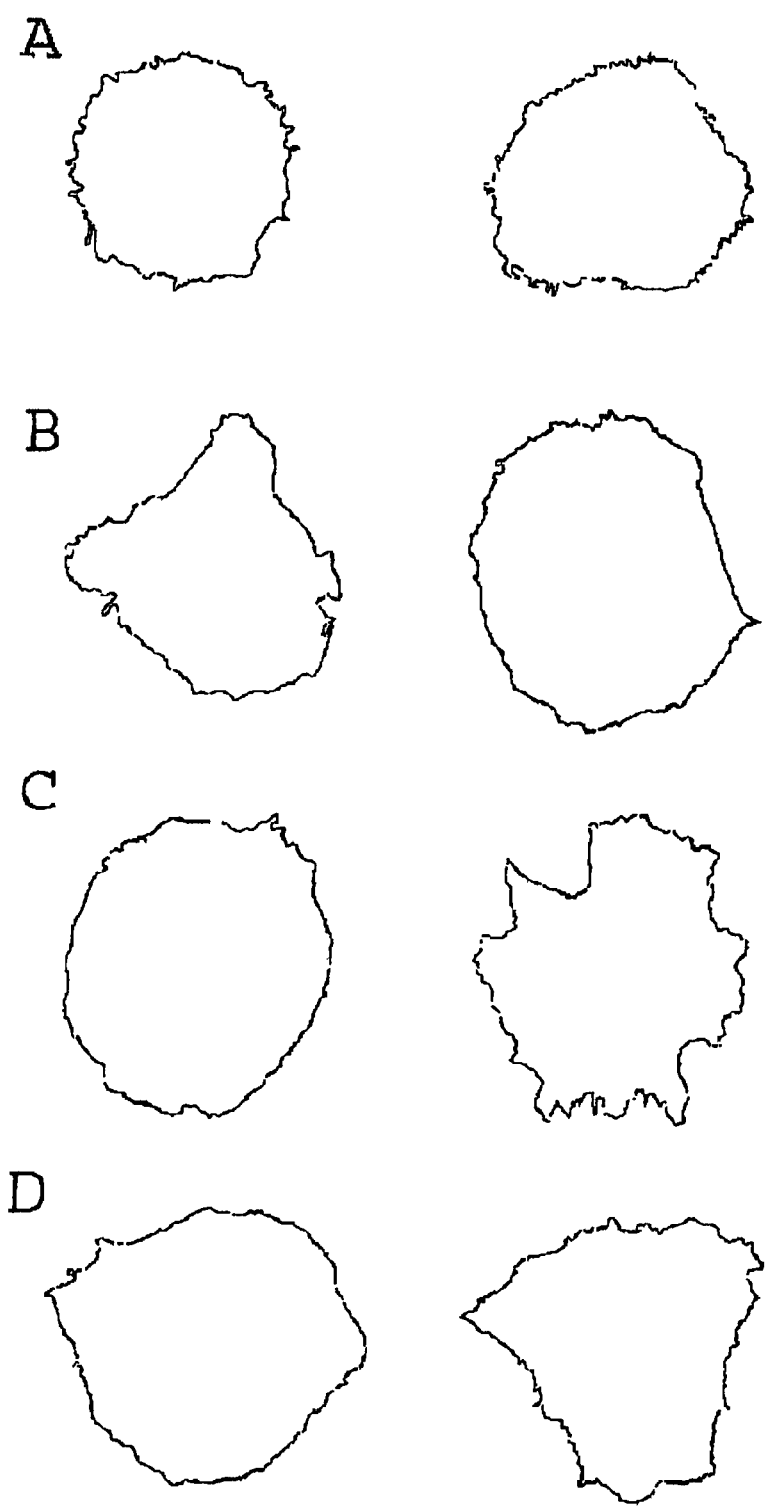
FIGS. 8A–8D are illustrations showing contours representing the cell edge that were obtained from scanning electron micrographs. They were extracted by computer software and then analyzed for the values of the variables that are relied upon in determining factor #4. 1000 W cells expressing different gene constructs or sets of constructs were injected as follows: A) GFP injection alone served as a control, B) cells co-injected with dnRho and GFP, C) cells co-injected with PAK and GFP, and D) cell co-injected with dnRho, PAK and GFP.

Cells overexpressing GFP and/or another gene construct were identified by epifluorescence microscopy. Points representing the perimeter were extracted from a TIF file and analyzed mathematically (7). Data sets made up of at least 30 cells were subjected to statistical analysis. Four types of contours extracted from such cells and TIF files are shown in FIG. 8. The variables that are heavily weighted in the computation of factor #4 include SHPF, PTOM, CSQD, FRNC, WDTH, MAXP, PSHR, and ASHR. The values of these descriptors increased or decreased in transformed and PMA-treated cells. Other descriptors that were less heavily weighted included MDAL, NONC, ALTI, FINE, CAVS, ACAV, and LCAV. Some of these values were changed on cells that were co-injected with dominant negative Rho and PAK (FIG. 9).

FIG. 9 shows the results of Tukey's test on values of CSQD and NONC for cells overexpressing genes for the proteins designated in FIG. 8. In addition, the PAK enzymatic blocker (PKB) and Rho GTPase activity blocker (CBC3) were introduced into certain cells. Samples enclosed by the same bracket are statistically indistinguishable. The resolution of cell samples overexpressing GFP, PAK and dominant negative Rho (PKR) indicate that sharp features have been reintroduced into cells such as those expressing GFP alone.

In addition to the method summarized in FIG. 9 being useful for basic research on the aberrations cancer cells, the method is also useful for assaying potential chemotherapy and chemopreventive drugs. Key values of several shape factors (F) are used in an equation to evaluate the cell's phenotype, for example:

$$Yhat = 476.31 + 72.1*F1 - 54.5*F2 - 67.5*F4 + 26.7*F7 + 21.7*F11 + 71.8*F12 - 18.0*F16$$

$$Yhat = 242.01 + 26.5*F1 - 11.7*F3 - 49.9*F4 + 21.2*F5 + 19.7*F7 + 14.5*F8 + 29.8*F12 - 27.7*F13$$

Since both of the cell lines used as subjects in the assay respond to taxane singly or in a combination with colchicine (FIG. 7) by acquiring sharper and/or longer features at the cell edge, variations in drugs composed from taxanes and mixtures of drugs including taxanes to achieve this effect are also within the scope of the present invention.

Reversal of the whole cancer cell phenotype is observed more rarely than the reversal of a single feature such as sharp features (F4). Since, in one cell line that is a subject of the assay, the overall reversal effect has been observed to be caused by exposure to one IC, substitution of another MT-depolymerizing agent for colchicine is also within the contemplated scope of the present invention. Further, synthesis of a portmanteau drug by combining paclitaxel and colchicine, and subsequently testing it as a chemotherapy or chemopreventive drug in humans is also within the scope of the present invention.

Still further, synthesis of a portmanteau drug, combining paclitaxel and any other MT-depolymerizing agent, in the hope of producing a chemotherapeutic or chemopreventive drug for cancer is also within the scope of the present invention. The index of efficacy for any such drug or drug combination is the results of an assay for phenotype based on cells' mass distribution and geometrical shape features. Another aspect of the present invention is, therefore, a practical method for detecting the efficacy of any drug or drug combination against cancer.

EXAMPLE III

Figure 10:
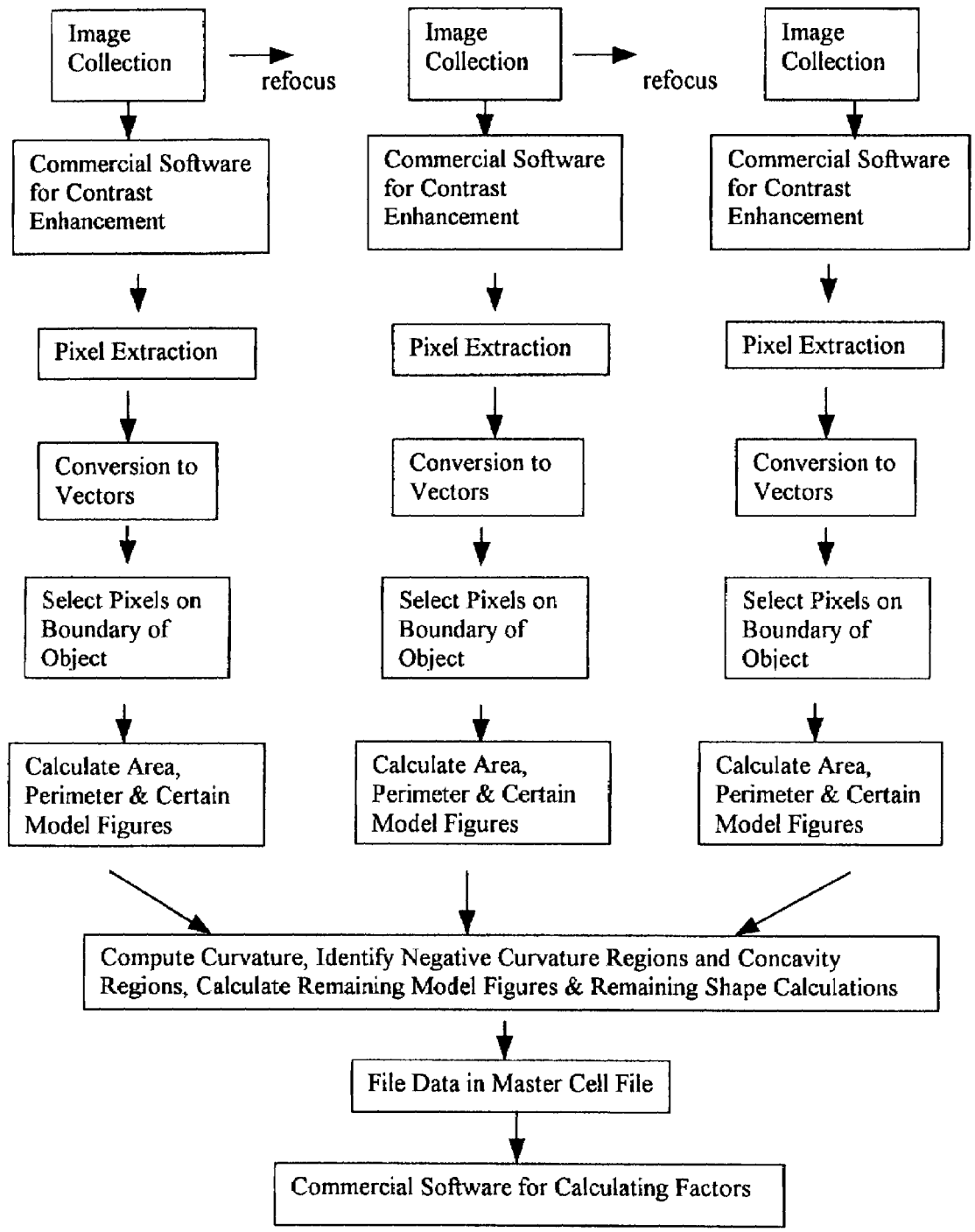
FIG. 10 is a data processing flow chart depicting assay mass distribution and architectural features in cells.

A flowchart showing the preferred method of image processing and segmentation is provided (FIG. 10). The extraction of latent factors from shape data is done in such a way that the new variables are qualitatively related to features which can be perceived by viewing the cells. The use of a large database of values for shape variables, as done herein, is desirable if factors are to be generated which approach this ideal. The definitions and names of highly correlated shape variables that contributed to a data set of exemplary factors are provided below. Here, the first 13 out of 20 factors could be given intuitive descriptions based on the variables they incorporated. Although certain factors beyond the 13th factor could also be given descriptive names, they became increasingly more contour-specific and more specific to a single kind of shape feature. Such intuitive factors can be used in interpreting alterations in cell shape characteristics that may be caused by exposing cells to a test drug or biological agent.

Factor #1 (having coarsely protruding or dissected areas in the higher contours)
  contour #1 ARAT, LCAV
  contour #2 SHPF, ARAT, FINE, ASHR, ACAV, LCAV
  contour #3 SHPF, ARAT, FINE, ASHR, ACAV, LCAV Factor #2 (having more or bigger protrusions in the second and third contours)
  contour #1 none
  contour #2 BMPS, MEDN, ALTI, SDFD, MAXP, MINP
  contour #3 BMPS, MEDN, ALTI, WDTH, FOCI, SDFD, MAXP, MINP Factor #3 (showing overall elongation of cell)
  contour #1 AXRT, CENT, SDCD
  contour #2 PTOM, AXRT, CENT, SDCD
  contour #3 PTOM, AXRT, CENT, SDCD Factor #4 (having elongated, triangular-shaped structures (filopodia) at cell edge)
  contour #1 SHPF, PTOM, CSQD, FRNC, WDTH, MAXP, ASHR, PSHR
  contour #2 none
  contour #3 none Factor #5 (having mass displacement (bulky projections or enlarged invaginations) at cell edge)
  contour #1 ARAT, SDWD, MDAL, SDCD, SDFD, FINE, ASHR, ACAV, LCAV
  contour #2 none
  contour #3 none Factor #6 (having hollowed-out areas in the third contour)
  contour #1 none
  contour #2 none
  contour #3 NONC, FRNC, SDNC, CAVS, CVSD Factor #7 (showing any regular scalloped structure at the cell edge)
  contour #1 LNNC, MEDN, ALTI, WDTH, MINP
  contour #2 none
  contour #3 none Factor #8 (showing spiked structures in the second contour)
  contour #1 none
  contour #2 CSQD, PSHR
  contour #3 none Factor #9 (tendency to tilt in the Z dimension (height))
  contour #1 DCNT
  contour #2 DCNT
  contour #3 DCNT Factor #10 (having knobby structures in the third contour)
  contour #1 none
  contour #2 none
  contour #3 SDMD, SDAL, SDWD Factor #11 (having knobby structures in the second contour)
  contour #1 none
  contour #2 SDMD, SDAL, SDWD
  contour #3 none Factor #12 (showing a steep rise of the cell edge off the substrate (rounding-up))
  contour #1 none
  contour #2 AFRN
  contour #3 AFRN Factor #13 (having large, hollowed-out areas in the second contour)
  contour #1 none
  contour #2 NONC, CAVS
  contour #3 none In certain preferred embodiment, the values of selected factors will be solved and used to predict properties or characteristics of any sample of cells presented as an unknown.

Throughout this application various publications are referenced by numerals within parenthesis. Full citations for these publications may be found at the end of this application, preceding the claims. The disclosure of these publications, and all publications mentioned herein, in their entireties are hereby incorporated by reference into this application in order to more fully describe the state of the art to which this invention pertains.

While this invention has been described with emphasis upon preferred embodiments, it would be obvious to those of ordinary skill in the art that preferred embodiments may be varied. It is intended that the invention may be practiced otherwise than as specifically described herein. Accordingly, this invention includes all modifications and claims spirit and scope of the appended claims.

REFERENCES

1. Heckman, C. A., Plummer, H. K., III and Runyeon, C. S., Persistent effects of phorbol 12-myristate 13-acetate: possible implication of vesicle traffic. J. Cell Physiol. 166: 217–230, 1996.
2. Holm, P. K., Eker, P., Sandvig, K. and van Deurs, B., Phorbol myristate acetate selectively stimulates apical endocytosis via protein kinase C in polarized MDCK cells. Exp. Cell Res. 217:157–168, 1995.
3. Heckman, C. A. and Jamasbi, R. J., Describing shape dynamics in transformed rat cells through latent factors. Exp. Cell Res. 246:69–82, 1999.
4. Olson, M. F., Ashworth, A. and Hall, A., An essential role for Rho, Rac, and Cdc42 GTPases in cell cycle progression through $G_1$, Science 269:1270–1272, 1995.
5. Kozma, R., Ahmed, S., Best, A. and Lim, L., The Ras-related protein Cdc42Hs and bradykinin promote formation of peripheral actin microspikes and filopodia in Swiss 3T3 fibroblasts. Mol. Cell Biol. 15:1942–1952, 1995.
6. Harden, N., Lee, J., Loh, H.-Y., Ohn, Y.-M., Tan, I., Leung, T., Manser, E. and Lim, L., A Drosophila homolog of the Rac- and Cdc42-activated serine/threonine kinase PAK is a potential focal adhesion and focal complex protein that colocalizes with dynamic actin structures, Mol. Cell Biol. 16:1896–1908, 1996.
7. Heckman, C. A., Campbell, A. E. and Wetzel, B., Characteristic shape and surface changes in epithelial transformation, Exp Cell Res. 169:127–148, 1987.
8. SAS Institute: SAS/STAT User's Guide. Version 6. Vol. 1. SAS Institute, Inc., Cary, N.C., p. 943, 1989.
9. Plummer, H. K., III, and Heckman, C. A., Transient expression of the transformed phenotype stimulated by 12-O-tetradecanoyl phorbol-13-acetate, Exp Cell Res. 188:66–74, 1990.
10. Rozengurt, E. and Mendoza, S., Monovalent ion fluxes and the control of cell proliferation in cultured fibroblasts. In: Growth Regulation by Ion Fluxes. Vol. 339. Leffert H L (ed). Ann NY Acad. Sci., PP 175–190, 1980.
11. Pressman, B. C., Ionophorous antibiotics as models for biological transport, Fed Proc 27:1283–1288, 1968.
12. Smith, J. B. and Rozengurt, E., Serum stimulates the $Na^+$, $K^+$ pump in quiescent fibroblasts by increasing $Na^+$ entry, Proc Natl. Acad. Sci. USA 75:5560–5564, 1978.

13. Roberts, R. L., Nath, J., Friedman, M. M. and Gallin, J. I., Effects of taxol on human neutrophils, J. Immunol. 129:2134–2141, 1982.
14. Ray, P., Middleton, W. and Berman, J., Mechanism of agonist-induced down-regulation and subsequent recovery of muscarinic acetylcholine receptors in a clonal neuroblastoma×glioma hybrid cell line, J. Neurochem. 52:402–409, 1989.
15. Herman, B. and Albertini, D. F., A time-lapse video image intensification analysis of cytoplasmic organelle movements during endosome translocation, J Cell Biol. 98:565–576, 1984.
16. Herman, B., Langevin, M. A. and Albertini, D. F., The effects of taxol on the organization of the cytoskeleton in cultured ovarian granulose cells, Eur. J. Cell Biol. 31:34–45, 1983.
17. Brown, D. L., Little, J. E., Chaly, N., Schweitzer, I. And Paulin-Levasseur, M., Effects of taxol on microtubule organization in mouse splenic lymphocytes and on response to mitogenic stimulation, Eur. J. Cell Biol. 37:130–139, 1985.
18. Pitterle, D. M., Sperling, R. T., Myers, M. G., Jr., White, M. F. and Blackshear, P. J., Early biochemical events in insulin-stimulated fluid phase endocytosis, Am J. Physiol. 276:E94-E105, 1999.
19. Hedin, U. and Thyberg, J., Receptor-mediated endocytosis of immunoglobulin-coated colloidal gold particles in cultured mouse peritoneal macrophages. Chloroquine and monensin inhibit transfer of the ligand from endocytic vesicles to lysosomes, Eur. J. Cell Biol. 39:130–135, 1985.
20. Porpaczy, Z., Tomasek, J. J. and Freeman, D. A., Internalized plasma membrane cholesterol passes through an endosome compartment that is distinct from the acid vesicle-lysosome compartment, Exp Cell Res. 234:217–224, 1997.
21. Wolkoff, A. W., Klausner, R. D., Ashwell, G. and Harford, J., Intracellular segregation of asialoglycoproteins and their receptor: a prelysosomal event subsequent to dissociation of the ligand-receptor complex, J Cell Biol. 98:375–381, 1984.
22. Jin, M. and Snider, M. D., Role of microtubules in transferring receptor transport from the cell surface to endosomes and the Golgi complex, J. Biol. Chem. 268: 18390–18397, 1993.
23. Stenseth, K. and Thyberg, J., Monensin and chloroquine inhibit transfer to lysosomes of endocytosed macromolecules in cultured mouse peritoneal macrophages, Eur. J. Cell Biol. 49:326–333, 1989.
24. Hamm-Alvarex, S. F, Kim, P. Y. and Sheetz, M. P., Regulation of vesicle transport in CV-1 cells and extracts, J. Cell Sci. 106:955–966, 1993.
25. Sheetz, M. P. and Yu, H., Regulation of kinesin and cytoplasmic dynein-driven organelle motility, Semin. Cell Dev. Biol. 7:329–334, 1996.
26. Touzani, K., Alvarado, F. and Vasseur, M., pH gradient effects on chloride transport across basolateral membrane vesicles from guinea-pig jejunum, J. Physiol. 500:385–400, 1997.
27. Goltz, J. S., Wolkoff, A. W., Novikoff, P. M., Stockert, R. J. and Satir, P., A role for microtubules in sorting endocytic vesicles in rat hepatocytes, Proc. Natl. Acad. Sci. USA 89:7026–7030, 1992.
28. Thatte, H. S., Bridges, K. R. and Golan, D. E., Microtubule inhibitors differentially affect translational movement, cell surface expression, and endocytosis of transferring receptors in K562 cells, J. Cell Physiol. 160: 345–357, 1994.
29. Hicke, L., Zanolari, B., Pypaert, M., Rohrer, J. and Riezman, H., Transport through the yeast endocytic pathway occurs through morphologically distinct compartments and requires an active secretory pathway and Sec 18p/N-ethylmaleimide-sensitive fusion protein, Mol. Biol. Cell 8:13–31, 1997.
30. Erickson, J. W., Zhang, C., Kahn, R. A., Evans, T. and Cerione, R. A., Mammalian Cdc42 is a brefeldin A-sensitive component of the Golgi apparatus, J. Biol. Chem. 271:26850–26854, 1996.
31. Novikof, P. M., Cammer, M., Tao, L., Oda, H., Stockert, R. J., Wolkoff, A. W. and Satir, P., Three-dimensional organization of rat hepatocyte cytoskeleton: relation to the asialoglycoprotein endocytosis pathway, J. Cell Sci. 109: 21–32, 1996.
32. Hamm-Alvarez, S. F., Layoff, B. E., Hummel, H. M., Kim, P. Y., Crews, A. L., Strauss, H. C. and Sheets, M. P., Coordinate depression of bradykinin receptor recycling and microtubule-dependent transport by taxol, Proc. Natl. Acad. Sci USA 91:7812–7816, 1994.
33. Somlyo, A. V. and Somlyo, A. P., From pharmacomechanical coupling to G-proteins and myosin phosphatase, Acta. Physiol. Scand. 164:437–448, 1998.
34. Lim, L., Manser, E., Leung, T. and Hall, C., Regulation of phosphorylation pathways by p21 GTPases: The p21 Ras-related Rho subfamily and its role in phosphorylation signaling pathways, Eur. J. Biochem. 242:171–185, 1996.
35. Aspenström, P., Effectors for the Rho GTPases, Curr. Opin. Cell Biol. 11:95–102, 1999.
36. Kolodney, M. S. and Elson, E. L., Contraction due to microtubule disruption is associated with increased phosphorylation of myosin regulatory light chain, Proc. Natl. Acad. Sci. USA 92:10252–10256, 1995.
37. Enomoto, T., Microtubule disruption induces the formation of actin stress fibers and focal adhesions in cultured cells: possible involvement of the rho signal cascade, Cell Struct. Funct. 21:317–326, 1996.
38. Ren, Y., Lin, R., Zheng, Y. and Busch, H., Cloning and characterization of GEF-H1, a microtubule-associated guanine nucleotide exchange factor for Rac and Rho GTPases, J. Biol. Chem. 273:34954–34960, 1998.
39. Gunderson, F. G. and Cook, T. A., Microtubules and signal transduction, Curr. Opin. Cell Biol. 11:81–94, 1999.
40. Grant, N. J. and Aunis, D., Effects of phorbol esters on cytoskeletal proteins in cultured bovine chromaffin cells: induction of neurofilament phosphorylation and reorganization of actin, Eur. J. Cell Biol. 52:36–46, 1990.
41. Vitale, M. L., Rodriquez Del Castillo, A. and Trifaro, J. M., Protein kinase C activation by phorbol esters induces chromaffin cell cortical filamentous actin disassembly and increases the initial rate of exocytosis in response to nicotinic receptor stimulation, Neuroscience 51:463–474, 1992.
42. Downey, G. P., Chan, C. K., Lea, P., Takai, A. and Grinstein, S., Phorbol ester-induced actin assembly in neutrophils: role of protein kinase C, J. Cell Biol. 116: 695–706, 1992.
43. Myrdal, S. E. and Auersperg, N., An agent or agents produced by virus-transformed cells cause unregulated ruffling in untransformed cells, J Cell Biol. 102:1224–1229, 1986.
44. Liu, W. S. and Heckman, C. A., The sevenfold way of PKC activation, Cell Signal 10:529–542, 998.

45. Hammon, S. mM., Jenco, J. M., Cadwallader, K., Cook, S., Frohman, M. A. and Morris, A. J., Characterization of phospholipase D1. Activation of the purified enzyme by phosphatidylinositol 4,5-bisphosphate, ARF and Rho family G-proteins and protein kinase C-α, J. Biol. Chem. 272:3860–3868, 1997.

46. Lopez, I., Burns, D. J. and Lambeth, J. D., Regulation of phospholipase D by protein kinase C in human neutrophils. Conventional isoforms of protein kinase C phosphorylate a phospholipase D-related component in the plasma membrane, J. Biol. Chem. 270:19465–19472, 1995.

47. Yamazaki, M., Zhang, Y., Watanabe, H., Yokozeki, T., Ohno, S., Kaibuchi, K., Shibata, H., Mukai, H., Ono, Y., Frohman, M. A. and Kanaho, Y., Interaction of the small G protein RhoA with the C terminus of human phopholipase Dl, J. Biol. Chem. 274:6035–6038, 1999.

48. Schonhorn, J. E., Akompong, T. and Wesslingresnick, M., Mechanism of transferring receptor down-regulation in K562 cells in response to protein-kinase-C activation, J. Biol. Chem. 270:3698–3705, 1995.

49. Schmalzing, G., Richter, H. P., Hansen, A., Schwarz, W., Just I and Aktories K: Involvement of the GTP-binding protein Rho in constitutive endocytosis in Xenopus laevus oocytes, J. Cell Biol. 130:1319–1332, 1995.

50. Swanson, J. A., Yirinec, B. D. and Silverstein, S. C., Phorbol esters and horseradish peroxidase stimulate pinocytosis and redirect the flow of pinocytosed fluid in macrophages, J. Cell Biol. 100:851–859, 1985.

51. Zacharias, U., He, C-J., Hagège, J., Xu, Y., Sraer, J-D, Brass, L. F. and Rondeau, E., Thrombin and phorbol ester induce internalization of thrombin receptor of human mesangial cells through different pathways, Exp. Cell Res. 216:371–379, 1995.

52. Niedergang, F., San-Jose, E., Rubin, B., Alarcon, B., Dautry-Varsat, A. and Alcover, A., Differential cytosolic tail dependence and intracellular fate of T-cell receptors internalized upon activation with superantigen or phorbol ester, Res. Immunol. 148:231–245, 1997.

53. Lenferink, A. E. G., Kramer, R. H., van Vugt, M. J. H., Königswieser, M., Di Fiore, P. P., van Zoelen, E. J. J. and van de Poll, M. L. M., Super-agonistic behaviour of epidermal growth factor/transforming growth factor-α chimaeras: correlation with receptor routing after ligand-induced internalization, Biochem. J. 327:859–865, 1997.

54. Ouyang, X. M., Gulliford, T., Huang, G. C. and Epstein, R. J., Transforming growth factor-alpha short-circuits downregulation of the epidermal growth factor receptor, J. Cell Physiol. 179:52–57, 1999.

55. Epstein, R. J., Gulliford, T. and Ouyang, X. M., The duration of phorbol-inducible ErbB2 tyrosine dephosphoryation parallels that of receptor endocytosis rather than threonine-686 phosphorylation: implications of the physiological role of protein kinase C in growth factor receptor signaling, Carcinogenesis 19:2013–2019, 1998.

56. Luo, Z. R. and Robinson, J. M., Colocaliztion of an endocytic marker and acid-phosphatase in a tubular reticular compartment in macrophages, J. Histochem. Cytochem. 40: 93–103, 1992.

57. Ruegg, C. L., Rajasekar, S., Stein, B. S. and Engleman, E. G., Degradation of CD4 following phorbol-induced internalization in human lymphocytes—T: evidence for distinct endocytic routing of CD4 and CD3, J. Biol. Chem. 267:18837–18843, 1992.

58. Kandror, K. V. and Pilch, P. F., Multiple endosomal recycling pathways in rat adipose cells, Biochem. J 331: 829–835, 1998.

59. Allen, L. A. and Aderem, A., Protein kinase C regulates MARCKS cycling between the plasma membrane and lysosomes in fibroblasts. EMBO J. 14:1109–1120, 1995.

60. Tseng, G. N., Zhu, B., Ling, S. and Yao, J. A., Quinidine enhances and suppresses Kvl. 2 from outside and inside the cell, respectively, J. Pharmacol. Exp. Ther. 279:844–855, 1996.

61. Grinde, B., Effect of carboxylic ionophores on lysosomal protein degradation in rat hepatocytes, Exp. Cell Res. 149:27–35, 1983.

62. Sahenk, Z. and Brown, A., Weak-base amines inhibit the anterograde-to-retrograde conversion of axonally transported vesicles in nerve terminals, J. Neurocytol. 20:365–375, 1991.

63. Rabkin, R., Hamik, A., Yagil, C., Hamel, F. G., Duckworth, W. C. and Fawcett, J., Processing of 125I-insulin by polarized cultured kidney cells, Exp. Cell Res. 224: 136–142, 1996.

64. Collins, C. A. and Vallee, R. B., Temperature-dependent reversible assembly of taxol-treated microtubules, J. Cell Biol. 105:2847–2854, 1987.

65. Thompson, W. C., Wilson, L. and Purich, D. L., Taxol induces microtubule assembly at low temperature, Cell Motil. 1: 445–454, 1981.

66. Bulinski, J. C., McGraw, T. E., Gruder, D., Nguyen, H. L. and Sheetz, M. P., Overexpression of MAP4 inhibits organelle motility and trafficking in vivo, J. Cell Sci. 110:3055–3064, 1997.

67. De Brabander, M., Geuens, G., Nuydens, R., Willebrords, R. and De Mey, J., Taxol induces the assembly of free microtubules in living cells and blocks the organizing capacity of the centrosomes and kinetochores, Proc. Natl. Acad. Sci. USA 78:5608–5612, 1981.

68. Sandoval, I. V., Bonifacino, J. S., Klausner, R. D., Henkart, M. and Wehland, J., Role of microtubules in the organization and localization of the Golgi apparatus, J. Cell Biol. 99:113–118, 1984.

69. White, M. F. and Kahn, C. R., The insulin signaling system, J. Biol. Chem. 269: 1–4, 1994.

70. Heidenreich, K. A., Zeppelin, T. and Robinson, L. J., Insulin and insulin-like growth factor I induce c-fos expression in postmitotic neurons by a protein kinase C-dependent pathway, J. Biol. Chem. 268:14663–14670, 1993.

71. Fumoleau, P., Delecroix, V., Perrocheau, G., Borg-Olivier, O., Maugard, C., Fety, R., Azli, N., Louboutin, J. P. and Riva, A., Clinical data by Navelbine—Taxotere association in breast cancer patients. Breast Cancer. In: Advances in Biology and Therapeutics. Calvo, F., Crépin, M. and Magdelenat, H. (eds). John Libbey Eurotext, Paris, pp273–278, 1996.

72. Heckman C A: Cell shape and growth control. Advances in Cell Culture, Maramorosch K, Ed. (Academic Press, N. Y.), 4: 85–156, 1985.

73. Heckman C A, Vroman L and Pitlick A: The nature of substrate-attached materials in human fibroblast cultures: localization of cell and fetal calf serum components. Tissue Cell 9: 317–334, 1977.

74. Olson A C, Larson N M and Heckman C A: Classification of cultured mammalian cells by shape analysis and pattern recognition. Proceedings National Academy Sciences USA 77: 1516–1520, 1980.

75. Heckman C A, Plummer H K, III and Mukherjee R: Enhancement of the transformed shape phenotype by microtubule inhibitors and reversal by an inhibitor combination. Int. J. Oncol. 16: 700–723, 2000.

76. Heckman C A, Olesen J B, Hasley J, Herber S and Boudreau N: Spatial mapping and analysis of chromatin imaged by computer assisted microscopy. J. Comp.-Assisted Microsc. 7: 235–252, 1995.
77. Heckman C A, Olesen J B, Love D S, Hasley J and Wales T S: Integration of a spatial map (SM) with transmission electron microscope (TEM) images of Drosophila polytene chromosome. (CD-Rom issue). J. Comp.-Assisted Microsc. 9: 211–221, 1997.
78. Olesen J B and Heckman C A: A 95 nm spacing in Drosophila polytene chromatin. Microsc. Microanal. 3: 311–320, 1997.
79. Kozma, R, Ahmed, S, Best, A, and Lim, L:The Ras-related protein Cdc42Hs and bradykinin promote formation of peripheral actin microspikes and filopodia in Swiss 3T3 fibroblasts. Mol Cell. Biol. 15: 1942–1952, 1995.
80. Nobes, C D and Hall, A: Rho, rac, and cdc42 GTPases regulate the assembly of multimolecular focal complexes associated with actin stress fibers, lamellipodia, and filopodia. Cell 81: 53–62, 1995.
81. Kozma, R, Sarner, S, Ahmed, S, and Lim, L: Rho family GTPases and neuronal growth cone remodeling: relationship between increased complexity induced by Cdc42Hs, Rac1, and acetylcholine and collapse induced by RhoA and lysophosphatidic acid. Mol. Cell. Biol. 17: 1201–1211, 1997.
82. Zhao, Z-S, Manser, E, Chen, X-Q, Chong, C, Leung, T, and Lim, L: A conserved negative regulatory region in aPAK: Inhibition of PAK kinases reveals their morphological roles downstream of Cdc42 and Rac1. Mol. Cell. Biol. 18: 2153–2163, 1998.
83. (same reference as #7).
84. Carlos, G., Braguer, D., Sabeur, G., Briand, C., 1998, "The effect of combining antitubulin agents on differentiated and undifferentiated human colon cancer cells" Anti-Cancer Drugs 9:209–221.
85. Campone, P., Fumoleau, P., Delecroix, V., Deporte-Fety, R., Perrocheau, G., Vermillet, L., Borg-Olivier, O., Louboutin, J. P., Bissery, M. C., Riva, A., Azli, N., 2001, "Phase I dose-finding and pharmacokinetic study of docetaxel and vinorelbine as first-line chemotherapy for metastatic breast cancer" Annals Oncology 12: 909–918.
86. Cohen, R. B., Mueller, S. C., Haden, K. and de Sousa, P. 2000, "Phase I study of weekly vinorelbine in combination with weekly paclitaxel in adult patients with advanced refractory cancer", Cancer Investigation 18: 422–428.

I claim:

1. A method for assaying the shape features of cells and determining whether the shape features are altered by exposure of the cells to a pharmaceutical or biological agent, comprising the steps of:
   (a) culturing at least two samples of a cell population, a first treated sample population being cultured in the presence of a test agent and a second untreated sample population being cultivated in the absence of the test agent,
   (b) generating a high-resolution image of each cell to be sampled from each of the sample populations as representative of the cultures, which image presents high contrast information in at least one contour of the cell or a portion of the cell, wherein the high contrast is generated at the cell edge or at least one or more interference contours, and the contrast is augmented by imaging processing,
   (c) extracting at least one contour from each cell or portion of a cell sampled from each of the sample populations,
   (d) extracting at least one boundary of at least one contour from each cell or portion of a cell that was sampled from each of the sample populations,
   (e) determining area, perimeter, and obtaining an equation for ellipse of concentration of the cell or portion of the cell and determining at least one or more variables representing shape features of the boundary or boundaries extracted from the contour or contours of one cell or portion of one cell,
   (f) repeating steps a-e for each cell sampled from each of the sample populations, and
   (g) determining whether any two populations of cells sampled, with and without exposure to test agent, differed from one another by using the values of the variables.

2. The method of claim 1, wherein high contrast is generated by imaging cells attached to a reflected light interferometer.

3. The method of claim 1, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

4. The method of claim 1, wherein at least one or more derived variables are based on different shape derived variables' values and the derived variables' values are used as a basis to compare the cells of a sample to reference values in a database.

5. The method of claim 1, wherein, in step (g), some or all variables' or derived variables' values are used to classify the cells and determining whether the cells of the sample of the sample population differ from cells of any other sample by steps including:
   (h) classifying the cells of treated and untreated sample populations by means of variables' or derived variables' values, wherein the comparison between the values from the samples is based upon reference values in a database, and such values used in a suitable classification equation including maximum likelihood estimation, multiple linear regression, and neural network,
   (i) determining the value of at least one statistic describing a characteristic of at least one sample of cells, and
   (j) determining that the untreated population that was sampled differs from the population treated with the pharmaceutical or biological agent, or comparing the variables' values for sampled cells against data in a database.

6. The method of claim 5, in which execution of the steps serves as a rapid assay for properties or characteristics of a cell significantly related to carcinogenesis or cancer.

7. The method of claim 5, in which execution of the steps serves as a rapid assay for an individual drug or a mixture of drugs, which drugs may reverse the cancer phenotype of cells, including:
   cells derived from liver, bile duct, or gall bladder including IAR20 PC1 cells;
   cells derived from respiratory airway lining including 1000W cell line, cells derived from other endodermal tissue origins in ontogeny including epithelial lining cells of the stomach, pancreas, intestine, urinary bladder, urethra, and thyroid gland; and, cells derived from ectodermal tissue origins in ontogeny including epithelial lining cells of esophagus, mouth, nasopharyngeal cavities, mammary gland.

8. The method of claim 5, in which execution of the steps serves as a rapid assay for the chemotherapeutic or chemopreventive effect of an individual drug or a mixture of drugs inhibiting development of cancer.

9. The method of claim 7, in which derived variables' values used to solve for a cancer-related phenotype of a cell include at least one of FACTOR1, FACTOR2, FACTOR3, FACTOR4, FACTOR5, FACTOR7, FACTOR8, FACTOR1, FACTOR12, FACTOR13, and FACTOR16.

10. The method of claim 5, wherein high contrast is generated by imaging cells attached to a reflected light interferometer.

11. The method of claim 5, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

12. The method of claim 5, wherein derived variables are based on different shape derived variables' values and the derived variables' values are used as a basis to compare the cells of a sample to reference values in a database.

13. The method of claim 4, wherein some or all variables' or derived variables' values are used to classify the cells and to determine whether the cells of the sample population differ from cells of any other sample by steps including:

(k) classifying the cells of treated and untreated samples by means of variables' or derived variables' values, wherein the comparison between the values from the samples is based upon reference values in a database, and such values used in a suitable classification equation, (l) determining the value of at least one statistic describing a characteristic of at least one sample of cells, and (m) determining that the untreated population that was sampled differs from the population treated with the pharmaceutical or biological agent, or comparing the variables' values for sampled cells against data in a database.

14. The method of claim 13, in which execution of the steps serves as a rapid assay for properties or characteristics of a cell significantly related to carcinogenesis or cancer.

15. The method of claim 13, in which execution of the steps serves as a rapid assay for an individual drug or a mixture of drugs, which drugs may reverse the cancer phenotype of cells, including:

cells derived from liver, bile duct, or gall bladder including IAR20 PC1 cells;

cells derived from respiratory airway lining including 1000 W cell line, cells derived from other endodermal tissue origins in ontogeny including epithelial lining cells of the stomach, pancreas, intestine, urinary bladder, urethra, and thyroid gland; and, cells derived from ectodermal tissue origins in ontogeny including epithelial lining cells of esophagus, mouth, nasopharyngeal cavities, mammary gland.

16. The method of claim 14, in which execution of the steps serves as a rapid assay for the chemotherapeutic or chemopreventive effect of an individual drug or a mixture of drugs inhibiting development of cancer.

17. The method of claim 15, in which derived variables' values used to solve for a cancer-related phenotype of a cell include at least one of FACTOR1, FACTOR2, FACTOR3, FACTOR4, FACTOR5, FACTOR7, FACTOR8, FACTOR11, FACTOR12, FACTOR13, and FACTOR16.

18. The method of claim 13, wherein high contrast is generated by imaging cells attached to a reflected light interferometer.

19. The method of claim 13, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

20. The method for assaying shape features of cells and determining whether the shape features are altered by exposure of the cells to a pharmaceutical or biological agent, wherein one or more of the steps are executed by an instruction set encoded as a program in software in a high-speed computer, comprising the steps of:

(a) culturing at least two samples of a cell population, a first treated sample population being cultured in the presence of a test agent and a second untreated sample population being cultivated in the absence of the test agent, (b) generating a high-resolution image of each cell to be sampled from each of the sample populations as representative of the cultures, which image presents high contrast information in at least one contour of the cell or a portion of the cell, wherein the high contrast is generated at the cell edge or at least one or more interference contours, and the contrast is augmented by imaging processing, (c) extracting at least one contour from each cell or portion of a cell sampled from each of the sample populations, (d) extracting at least one boundary of at least one contour from each cell or portion of a cell that was sampled from each of the sample populations, (e) determining area, perimeter, and obtaining an equation for ellipse of concentration of the cell or portion of the cell and determining at least one or more variables representing shape features of the boundary or boundaries extracted from the contour or contours of one cell or portion of one cell, (f) repeating steps a–e for each cell sampled from each of the sample populations, and (g) determining whether any two populations of cells sampled, with and without exposure to test agent, differed from one another;

wherein one or more of the steps are executed by an instruction set encoded as a program in software in a high-speed computer, comprising:

(h) focusing of the cell or a portion of the cell at the level of at least one contour while an image is captured in a charge-coupled device or video camera and written in a recognized software format in computer memory, (i) processing a single image or a series of images of the cell or portion of the cell by at least one of a series of image processing algorithms including edge enhancement and thresholding, (j) separating pixels representing a contour or repeated contours of the cell or portion of the cell from the pixels representing background, (k) extracting a boundary on the contour or contours from among the pixels representing an image of the contour(s) of a cell or portion of a cell, (l) determining values of an equation of ellipse of concentration and at least one dimensioned variable and determining the value of at least one dimensionless shape variable reflecting shape features of at least one boundary on the cell or portion of the cell, (m) combining the values of the variables into a data set representative of at least a sampled population from the treated and untreated groups, and (n) determining whether the cells of the unknown and known samples show a significant difference.

21. The method of claim 20, in which execution of at least two of the steps is directed by a script to automate extraction of a boundary or boundaries from at least one contour of the cell or portion of the cell and/or the determination of at least one dimensioned and at least one dimensionless feature from the boundary or boundaries.

22. The method of claim 21, further including determining whether the cells of unknown and known samples show any discernable difference.

23. The method of claim 20, in which a program stream and lists of input files and output files, along with an optional cache for error messages, are represented by icons on a graphical user interface.

24. The method of claim 20, in which execution of the steps serves as a rapid assay for properties or characteristics of a cell significantly related to carcinogenesis or cancer.

25. The method of claim 20, in which execution of the steps serves as a rapid assay for an individual drug or a mixture of drugs, which drugs may reverse the cancer phenotype of cells, including:
cells derived from liver, bile duct, or gall bladder including IAR20 PC1 cells;
cells derived from respiratory airway lining including 1000 W cell line,
cells derived from other endodermal tissue origins in ontogeny including epithelial lining cells of the stomach, pancreas, colon; and,
cells derived from ectodermal tissue origins in ontogeny including epithelial lining cells of esophagus, mouth, nasopharyngeal cavities, mammary gland.

26. The method of claim 20, in which execution of the steps serves as a rapid assay for the chemotherapeutic or chemopreventive effect of an individual drug or a mixture of drugs inhibiting development of cancer.

27. The method of claim 25, in which derived variables' values used to solve for a cancer-related phenotype of a cell include at least one of FACTOR1, FACTOR2, FACTOR3, FACTOR4, FACTOR5, FACTOR7, FACTOR8, FACTOR11, FACTOR12, FACTOR13, and FACTOR16.

28. The method of claim 20, wherein high contrast is generated by imaging cells attached to a reflected light interferometer.

29. The method of claim 20, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

30. The method of claim 20, wherein derived variables are based on different shape derived variables' values and the derived variables' values are used as a basis to compare the cells of a sample to reference values in a database.

31. The method of claim 20, in which execution of the steps serves as a rapid assay for properties or characteristics of a cell significantly related to carcinogenesis or cancer.

32. The method of claim 20, wherein, in step (g), some or all variables' or derived variables' values are used to classify the cells and determining whether the cells of the sample population differ from cells of any other sample by steps including:

(o) classifying the cells of treated and untreated sample populations by means of variables' or derived variables' values, wherein the comparison between the values from the samples is based upon reference values in a database, and such values used in a suitable classification equation including maximum likelihood estimation, multiple linear regression, and neural network, (p) determining the value of at least one statistic describing a characteristic of at least one sample of cells, and (q) determining that the untreated population that was sampled differs from the population treated with the pharmaceutical or biological agent, or comparing the variables' values for sampled cells against data in a database.

33. The method of claim 32, in which execution of the steps serves as a rapid assay for properties or characteristics of a cell significantly related to carcinogenesis or cancer.

34. The method of claim 32, in which execution of the steps serves as a rapid assay for an individual drug or a mixture of drugs, which drugs may reverse the cancer phenotype of cells, including: cells derived from liver, bile duct, or gall bladder including IAR20 PC1 cells;
cells derived from respiratory airway lining including 1000W cell line, cells derived from other endodermal tissue origins in ontogeny including epithelial lining cells of the stomach, pancreas, colon; and,
cells derived from ectodermal tissue origins in ontogeny including epithelial lining cells of esophagus, mouth, nasopharyngeal cavities, mammary gland.

35. The method of claim 32, in which execution of the steps serves as a rapid assay for the chemotherapeutic or chemopreventive effect of an individual drug or a mixture of drugs inhibiting development of cancer.

36. The method of claim 34, in which derived variables' values used to solve for a cancer-related phenotype of a cell include at least one of FACTOR1, FACTOR2, FACTOR3, FACTOR4, FACTOR5, FACTOR7, FACTOR8, FACTOR11, FACTOR12, FACTOR13, and FACTOR16.

37. The method of claim 32, wherein high contrast is generated by imaging cells attached to a reflected light interferometer.

38. The method of claim 32, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

39. The method of claim 32, wherein derived variables are based on different shape derived variables' values and the derived variables' values are used as a basis to compare the cells of a sample to reference values in a database.

40. The method of claim 30, wherein some or all variables' or derived variables' values are used to classify the cells and to determine whether the cells of the sample population differ from cells of any other sample by steps including:
(r) classifying the cells of treated and untreated samples by means of variables' or derived variables' values, wherein the comparison between the values from the samples is based upon reference values in a database, and such values used in a suitable classification equation,
(s) determining the value of at least one statistic describing a characteristic of at least one sample of cells, and
(t) determining that the untreated population that was sampled differs from the population treated with the pharmaceutical or biological agent, or comparing the variables' values for sampled cells against data in a database.

41. The method of claim 40, in which execution of the steps serves as a rapid assay for properties or characteristics of a cell significantly related to carcinogenesis or cancer.

42. The method of claim 40, in which execution of the steps serves as a rapid assay for an individual drug or a mixture of drugs, which drugs may reverse the cancer phenotype of cells, including:
cells derived from liver, bile duct, or gall bladder including IAR20 PC1 cells;
cells derived from respiratory airway lining including 1000 W cell line,
cells derived from other endodermal tissue origins in ontogeny including epithelial lining cells of the stomach, pancreas, colon; and,
cells derived from ectodermal tissue origins in ontogeny including epithelial lining cells of esophagus, mouth, nasopharyngeal cavities, mammary gland.

43. The method of claim 42, in which execution of the steps serves as a rapid assay for the chemotherapeutic or chemopreventive effect of an individual drug or a mixture of drugs inhibiting development of cancer.

44. The method of claim 42, in which at least one or more derived variables' values used to solve for a cancer-related phenotype of a cell include at least one of FACTOR1, FACTOR2, FACTOR3, FACTOR4, FACTOR5, FACTOR7, FACTOR8, FACTOR11, FACTOR12, FACTOR13, and FACTOR16.

45. The method of claim 40, wherein high contrast is generated by imaging cells attached to a reflected light interferometer.

46. The method of claim 40, wherein values of one or more of the following dimensionless variables are determined: OCNT, SHPF, PTOM, AXRT, ARAT, AFRN, DCNT, ANGL, CURV, CSQD, NONC, FRNC, LNNC, SDNC, BMPS, MEDN, SDMD, ALTI, SDAL, WDTH, SDWD, MDAL, CENT, SDCD, FOCI, SDFD, FINE, MAXP, MINP, ASHR, PHSR, CAVS, ACAV, CVSD, LCAV and their values used to compare the cells of the sample population to reference values in a database.

* * * * *

UNITED STATES PATENT AND TRADEMARK OFFICE
CERTIFICATE OF CORRECTION

PATENT NO. : 7,050,620 B2
APPLICATION NO. : 10/109394
DATED : May 23, 2006
INVENTOR(S) : Carol A. Heckman It is certified that error appears in the above-identified patent and that said Letters Patent is hereby corrected as shown below:

In column 39, line 15, please delete "FACTOR1" and replace with - - FACTOR11 - -.

Signed and Sealed this

Fifteenth Day of August, 2006

JON W. DUDAS
*Director of the United States Patent and Trademark Office*